United States Patent
Hunter et al.

(10) Patent No.: US 12,249,432 B2
(45) Date of Patent: *Mar. 11, 2025

(54) REMOTE HEALTHCARE COMMUNICATION SYSTEMS AND METHODS

(71) Applicant: Mycare Integrated Software Solutions, LLC, Oklahoma City, OK (US)

(72) Inventors: Jeff Hunter, Oklahoma City, OK (US); Jeremy Hume, Oklahoma City, OK (US)

(73) Assignee: Mycare Integrated Software Solutions, LLC, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,791

(22) Filed: Apr. 25, 2023

(65) Prior Publication Data

US 2023/0260667 A1 Aug. 17, 2023

Related U.S. Application Data

(63) Continuation of application No. 16/703,557, filed on Dec. 4, 2019, now Pat. No. 11,670,427.

(Continued)

(51) Int. Cl.
*G16H 80/00* (2018.01)
*G06F 3/0482* (2013.01)
*G06F 16/51* (2019.01)
*G06F 21/60* (2013.01)
*G06Q 30/04* (2012.01)
*G06Q 50/26* (2024.01)
*G16H 10/60* (2018.01)
*G16H 40/67* (2018.01)
*H04L 65/1093* (2022.01)

(Continued)

(52) U.S. Cl.
CPC ............. *G16H 80/00* (2018.01); *G06F 16/51* (2019.01); *G06F 21/602* (2013.01); *G06Q 30/04* (2013.01); *G06Q 50/265* (2013.01); *G16H 10/60* (2018.01); *G16H 40/67* (2018.01); *H04L 65/1093* (2013.01); *H04L 65/75* (2022.05); *H04N 7/147* (2013.01); *H04N 7/155* (2013.01); *H04W 4/029* (2018.02); *G06F 3/0482* (2013.01)

(58) Field of Classification Search
None
See application file for complete search history.

(56) References Cited

U.S. PATENT DOCUMENTS 6,944,536 B2   9/2005  Singleton
7,733,224 B2   6/2010  Tran
(Continued)

*Primary Examiner* — Hemant S Patel
(74) *Attorney, Agent, or Firm* — DUNLAP CODDING, P.C.

(57) ABSTRACT

A remote healthcare system is described. The remote healthcare system includes a system interface that includes patient and user interfaces in the form of electronic device applications that are accessed by a patient and a user, respectively. The remote healthcare communication system enables secure, HIPAA compliant phone, video, and data-sharing between the patient and user. During a video session, the user may be able to access the patient's medical records and/or other patient health-related data.

15 Claims, 17 Drawing Sheets

Related U.S. Application Data

(60) Provisional application No. 62/775,256, filed on Dec. 4, 2018.

(51) Int. Cl.
    *H04L 65/75*      (2022.01)
    *H04N 7/14*       (2006.01)
    *H04N 7/15*       (2006.01)
    *H04W 4/029*     (2018.01)

(56) References Cited

U.S. PATENT DOCUMENTS

| | | | |
|---|---|---|---|
| 8,126,735 B2 * | 2/2012 | Dicks | G06Q 10/10 710/16 |
| 11,670,427 B2 * | 6/2023 | Hunter | H04L 65/1063 705/3 |
| 2001/0051765 A1 | 12/2001 | Walker et al. | |
| 2009/0292555 A1 | 11/2009 | Brown | |
| 2013/0060576 A1 * | 3/2013 | Hamm | G16H 40/67 705/2 |
| 2015/0116126 A1 * | 4/2015 | Hyde | G01D 4/02 340/870.02 |
| 2016/0088257 A1 * | 3/2016 | Kim | G16H 10/60 348/14.07 |
| 2017/0300647 A1 * | 10/2017 | Goldberg | G16H 20/10 |
| 2018/0065026 A1 * | 3/2018 | Ray | A63B 22/02 |
| 2020/0066414 A1 * | 2/2020 | Neff | H04L 12/1818 |

* cited by examiner

My Health

| Height | Update |
| Weight --- Last 282lbs | Update |
| Blood Pressure --- Last 140/95 | Update |
| Blood Sugar --- Last 95 | Update |
| Exercise Log | Update |
| Eating Log | Update |

FIG. 3B

My Team

- Betty LCMS — Connect
- John RN — Connect
- Joe RSS — Connect

Crisis

FIG. 3C

Patient select crisis button

Data-triggered selection of crisis button

REMOTE HEALTHCARE COMMUNICATION SYSTEMS AND METHODS

CROSS-REFERENCE TO RELATED APPLICATIONS

The present patent application is a continuation of and claims priority to the patent application identified by U.S. Ser. No. 16/703,557, filed Dec. 4, 2019, which claims priority to the provisional patent application identified by U.S. Ser. No. 62/775,256, filed on Dec. 4, 2018 the entire contents of all of which are hereby incorporated herein by reference.

FIELD OF THE DISCLOSURE

The presently disclosed and/or claimed inventive concept(s) relates, in general, to a remote healthcare system that improves services provided to mental health patients, and thus the care received by mental health patients. More particularly the presently disclosed and/or claimed inventive concept(s) relates to a comprehensive remote healthcare system involving various communication systems, integrated medical data, data viewing systems, and emergency response protocols for mental health patient retention and treatment.

BACKGROUND

The mental health industry faces numerous challenges regarding proper treatment for patients. In particular, communication between medical professionals and patients and comprehensive patient assessments play critical roles in effective medical treatment.

Conventional approaches to mental health care involve visits to health care facilities in order to receive treatment. However, patients who require mental health care often cannot get access when they need it or, in many cases, choose not to seek treatment. Reasons for such non-attendance include: (i) patients may not be located near a mental health care facility; (ii) patients may be housebound or have trouble lining up childcare; (iii) cost of in-person visits; and (iv) patients don't prioritize or make time for mental health care. Additionally, in emergency situations, mental health patients may not know who to contact and/or how to contact the appropriate person—e.g., a medical professional, medical staff, emergency responder, family member, friend, or otherwise. For these and other reasons, the inventors have found that mental health patients have difficulty adhering to treatment plans and that communication often breaks down between medical professionals and patients.

Recently, remote health systems such as telemedicine systems have been developed to address the physical separation between medical professionals and patients. Telemedicine generally refers to the practice of using telecommunications technology to evaluate, diagnose, and care for patients at a distance. While telemedicine systems address some limitations to effective medical treatment such as physical location, transportation, and convenience, existing telemedicine systems lack features for comprehensive patient care, communication during emergencies, communication with third parties, the feel of an in-person visit, and alternative and/or improved manners of interaction for both the patient and medical professional. In conventional telemedicine systems, communications between patient and medical professional are often being conducted without the benefit of the patient's medical history being available to the professional. Additionally, existing telemedicine systems also lack the capability to provide an integrated remote patient care environment, allowing remote monitoring to be seamlessly combined with analysis of patient information and feedback from health care providers and the patient themselves.

For these and other reasons, the inventors have found that an improved remote healthcare system involving various communication systems, integrated medical data, improved data viewing systems, and emergency response protocols improves mental health patient retention and outcomes. It is to such an improved remote healthcare system that the present disclosure is directed.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing. It is to be noted that the appended drawings illustrate only typical embodiments of this disclosure and are therefore not to be considered limiting in scope, for the disclosure may admit to other equally-effective embodiments. In the drawings:

FIG. 3A, 3B, 3C illustrate diagrammatic views of an example patient interface with graphical user interface screens thereon when no video conference session is active.

DETAILED DESCRIPTION

Figure 1:
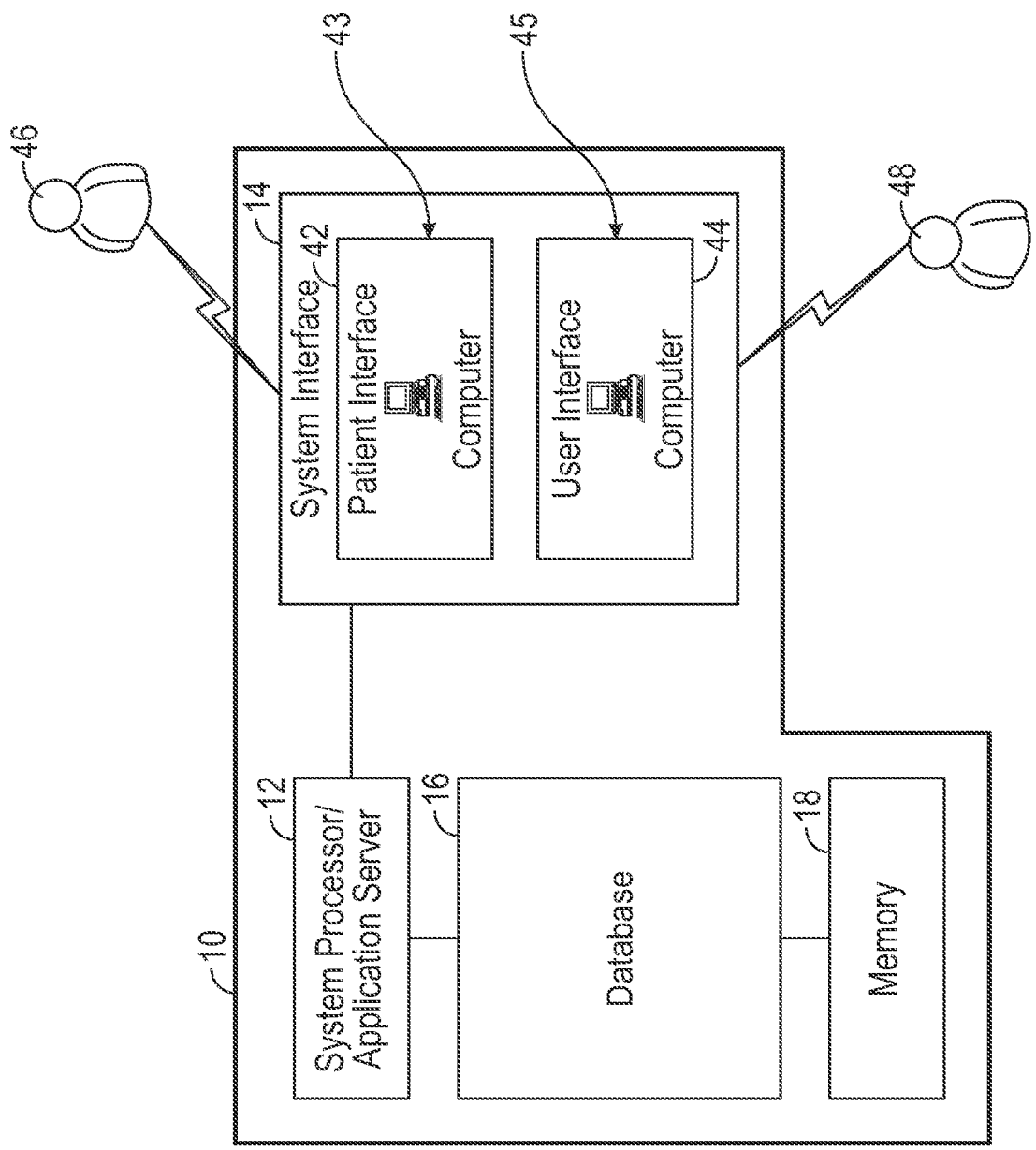
FIG. 1 is a block diagram of one embodiment of the system for remote healthcare communication in accordance with the present disclosure.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description only and should not be regarded as limiting.

Unless otherwise defined herein, mechanical and technical terms used in connection with the present disclosure shall have the meanings that are commonly understood by those of ordinary skill in the art. Further, unless otherwise required by context, singular terms shall include pluralities and plural terms shall include the singular.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a sensor" may refer to one or more sensors, two or more sensors, three or more sensors, four or more sensors, or greater numbers of sensors. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims or specification is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for an apparatus/device/system/kit, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent or less from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), field programmable gate array (FPGA), a combination of hardware and software, and/or the like. The term "processor" as used herein means a single processor or multiple processors working independently or together to collectively perform a task.

A "module" in software is a part of a program. Programs are composed of one or more independently developed modules that are not combined until the program is linked. A single module can contain one or several routines or steps. A "module" in hardware, is a self-contained component.

Software may include one or more computer readable instructions that when executed by one or more components cause the component to perform a specified function. It should be understood that the algorithms described herein may be stored on one or more non-transitory computer readable medium. Exemplary non-transitory computer readable mediums may include random access memory, read only memory, flash memory, and/or the like. Such non-transitory computer readable mediums may be electrically based, optically based, and/or the like.

A "software application" is a program or group of programs designed for end users. Application software can be divided into two general classes: systems software and applications software. Systems software include low-level programs that interact with the computer at a very basic level. This includes operating systems, compilers, and utilities for managing computer resources. In contrast, applications software (also called end-user programs) includes database programs, word processors, and spreadsheets. Figuratively speaking, applications software uses and interacts with the systems software because the applications software is unable to run without the operating system and system utilities of the systems software.

A "software module" is a file or group of files that work together to perform at least one function. The file or group of files contain instructions. "Module" implies a single executable file that is only a part of the application, such as a DLL. When referring to an entire program, the terms "application" and "software program" are typically used. A software module is defined as a series of process steps stored in an electronic memory of an electronic device and executed by the system processor of an electronic device such as a computer, tablet, smart phone, or other equivalent device known in the prior art.

A "software application module" is a program or group of programs designed for end users that contains one or more files that contain instructions to be executed by a computer or other equivalent device.

A "User" is any person using the computer system executing the method of the present invention. With regards to one or more embodiments of the present system, the term "user" is synonymous with "healthcare professional."

The presently disclosed and/or claimed inventive concept(s) is a technological solution to the problems described above involving communication between medical professionals and patients and comprehensive patient assessments for effective health treatment. In one embodiment, the remote healthcare communication system is especially adapted for use in therapy sessions with patients requiring mental health care. Generally, the remote healthcare communication system comprises a system interface that includes patient and user interfaces in the form of electronic device applications that are accessed by a patient and a user, respectively. The remote healthcare communication system enables secure, HIPAA compliant phone, video, and data-sharing between the patient and user. During a video session, the user may be able to access the patient's medical records and/or other patient health-related data. The video functionality may also include an overlay screen such that the user may review the patient's medical records and/or other patient health-related data and take notes about the session without breaking eye contact with the patient. During and following a video session, the user may easily document the session through the use of various means of displaying information or inputting data to complete a session record 84 that is kept for each session. Additionally, a Session Documenter feature automatically captures and stores still images of the video call.

In certain embodiments, the remote healthcare communication system further comprises a system processor and application server and one or more database(s) that collect, process, and store data from the patient and user. In some embodiments, comprehensive patient-related information may be catalogued within the one or more database(s) for retrieval and/or analysis. For example, patient behavioral and biological information may be catalogued. In some embodiments, such information may be stored in one or more database with measurements of data associated therewith, in addition to other metadata associated with the information and/or data (e.g., date, algorithms used).

Data may be collected from the patient directly or indirectly. The collection of data from the patient allows: (1) medical professionals (and/or others involved in the patient's healthcare) to monitor and adjust out-of-office prescriptions and written regimens; (2) medical professionals (and/or others involved in the patient's healthcare) address patient care for patients who are geographically remote; (3) others involved in the patient's healthcare, such as family and/or friends and/or people selected by the patient, to have direct contact with the patient and/or the medical professional; and (4) enhanced patient's effectiveness during home programming by having visual and written interaction with medical professionals (and/or others involved in the patient's healthcare).

In certain embodiments, the remote healthcare communication system further comprises a system interface that includes a first responder interface in the form of an electronic device application that is accessed by a first responder. The first responder electronic device application contains location identifier capabilities such that crisis calls to first responders may be routed appropriately.

In another embodiment, the remote healthcare communication system further comprises a system interface that includes a support group interface 54 in the form of an electronic device application that is accessed by a member of a patient's support group. The remote healthcare communication system enables secure, HIPAA compliant phone, video, and data-sharing between the patient and member of the patient's support group. The remote healthcare communication system may also enable three-way calling between the patient, member of the patient's support group, and a user.

System Design

Figure 2:
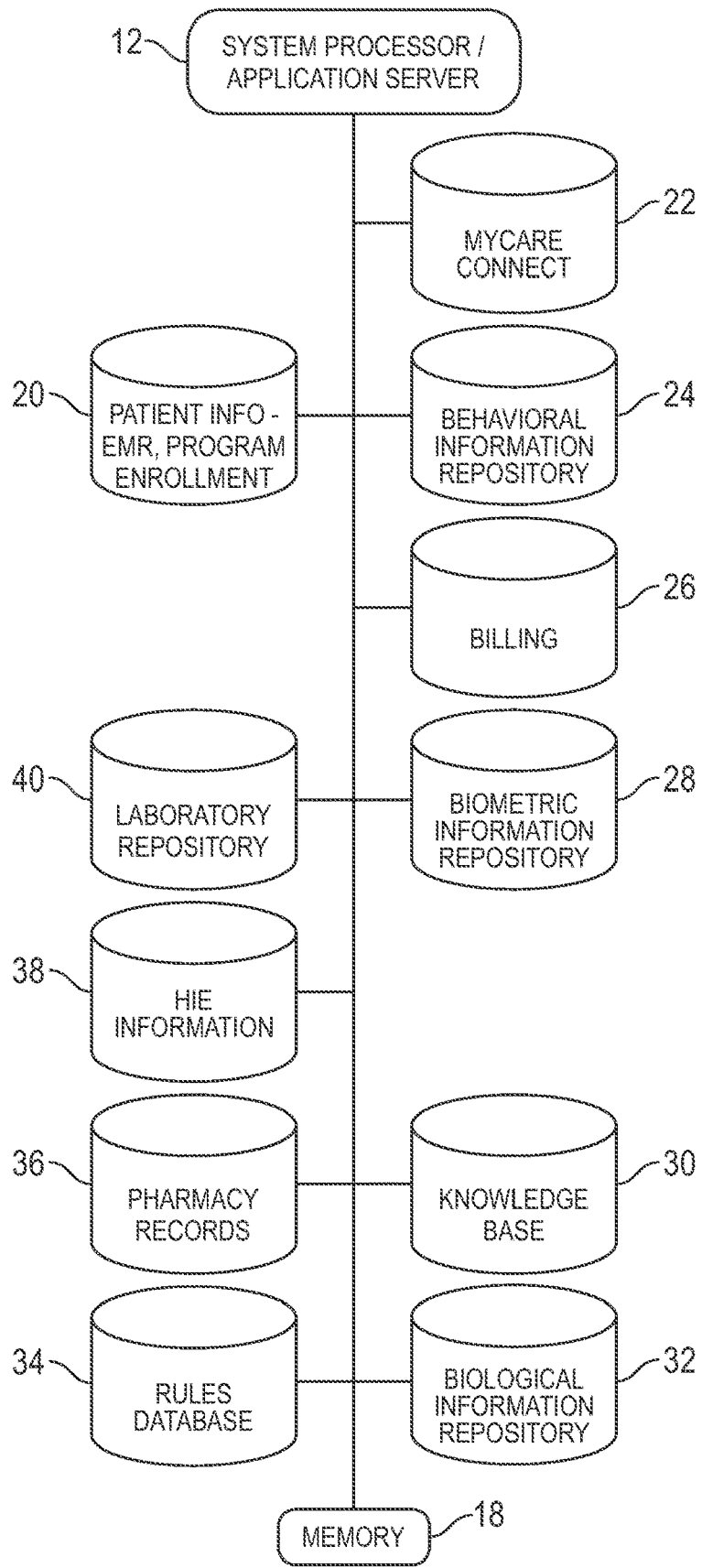
FIG. 2 is a block diagram of one embodiment of the one or more database(s) in the system for remote healthcare communication in accordance with the present disclosure.

Referring now to the Figures, and in particular to FIG. 1, shown therein is a block diagram depicting an exemplary system for remote healthcare communication according to the instant disclosure. This system may be used in conjunction with the methods described in FIGS. 8-12, as well as any subset or combination of the elements thereof. The remote healthcare communication system 10 comprises a system processor and application server 12 in communication with a system interface 14 and one or more database(s) 16 stored in a non-transitory memory 18. The system processor and application server 12 retrieves and executes instructions stored in the memory 18 to control the operation of the remote healthcare communication system 10. The system interface 14 communicates bi-directionally with the application server 12 by way of a communication link. The communication link may be formed of optical links, conductive links, wireless links, and combinations thereof. Referring now to FIG. 2, in one embodiment, the one or more database(s) 16 may be stored in the memory 18, and be characterized as a Patient Information Repository 20, a MyCare Connect 22, a Behavioral Information Repository 24, a Billing repository 26, a Biometric Information Repository 28, a Knowledge Base 30, a Biological Information Repository 32, a Rules Database 34, a Pharmacy Records Repository 36, a Health Information Exchange (HIE) Information 38, and a Laboratory Repository 40.

The system interface 14 shown in FIG. 1 includes patient and user electronic devices 43, 45 (such as an iPad, smartphone, computer, or the like that includes at least one processor, a display, an input unit (e.g., a touch screen), a microphone, a speaker, and a communication interface such as a wireless transceiver). The patient and user electronic devices 43, 45 comprising a patient interface 42 and a user interface 44 in the form of electronic device applications that run on the at least one processor of the electronic devices 43, 45, and that are accessed by a patient 46 and user 48, respectively. In certain embodiments, the system interface 14 further includes a first responder interface 50 in the form of an electronic device application running on an electronic device (not shown) that is similar in construction to the patient and user devices 43, 45. The first responder interface 50 is accessed by a first responder 52. In another non-limiting embodiment, the system interface 14 further includes a support group interface 54 in the form of an electronic device application that is accessed by a member of a patient's support group 56.

System Operation

Figure 3A:
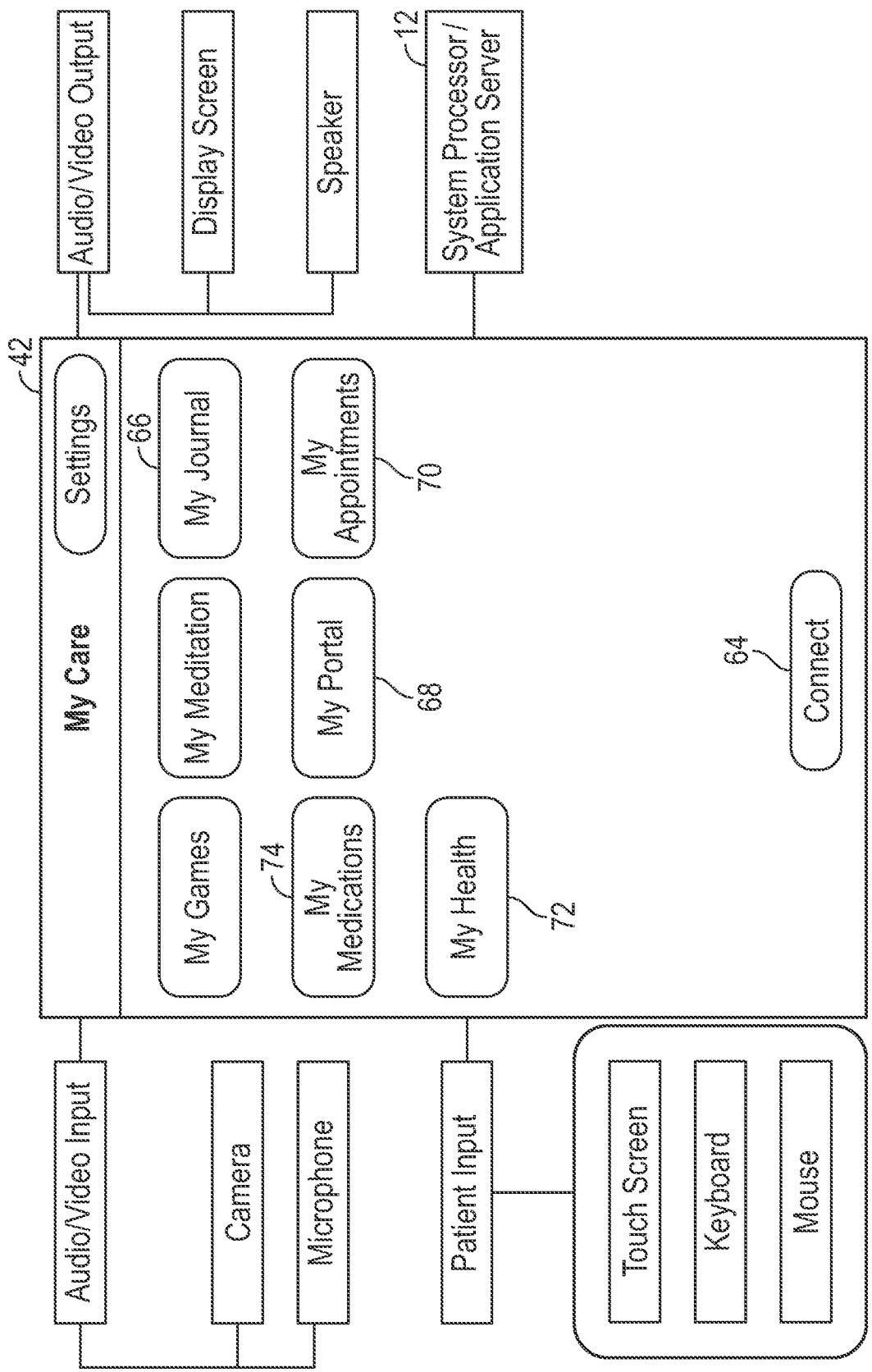
Figure 4:
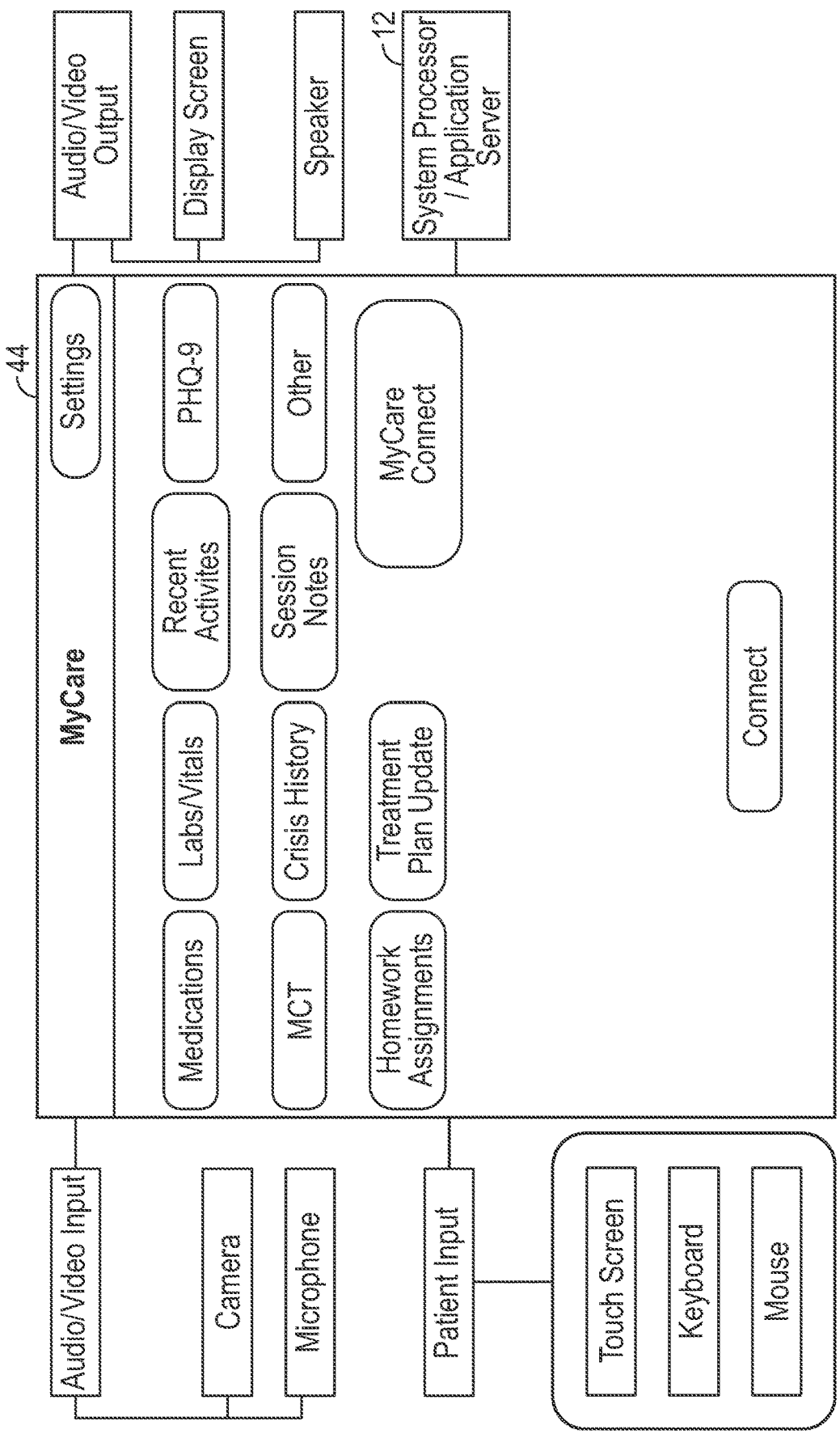
FIG. 4 illustrates a diagrammatic view of an example user interface with graphical user interface screens thereon when no video conference session is active.

In operation, the patient 46 is enrolled in a mental health care program that is based on the patient's mental health level and under the care of the user 48. The patient's mental health care program (and information regarding such) is stored the memory 18. The user 48 prescribes a therapy program to the patient 46. The therapy program is encoded by an application on the patient electronic device 43 and displayed to the patient 46 via the patient interface 42. For example, but not by way of limitation, the patient interface 42 may display selections chosen from crisis 62 (not shown), connect 64, journal 66, portal 68, appointments 70, health 72, medications 74, games, meditation, and settings as shown in FIG. 3A.

The patient electronic device 43 receives data from the user 48 through the patient interface 42 regarding the patient's health information and care, which data is transmitted to the application server 12 and stored in the memory 18. The patient electronic device 43 may also provide data from the patient 46 to the user 48 through the patient interface 42. The patient electronic device 43 may also receive data automatically through the patient interface 42 from a preprogrammed application existing on the patient electronic device 43 and may be based on, for example, information stored in the one or more database(s) 16 or the data received from the patient 46.

The user electronic device 45 receives data from the patient 46 through the user interface 44 regarding the patient's health information and care. The user electronic device 45 may also provide data from the user 48 to the patient 46 through the user interface 44. For example, a user 48 can select any screening, task, or function and assign the screening, task, or function (collectively referred to herein as a "task") to the patient 46. The patient electronic device 43 receives the task, where the task is accessible by the patient 46 through the patient interface 42. The patient interface 42 may alert the patient 46 upon receiving a new task. Once the task is complete, the user 48 may be notified. In the event that the result of the task falls outside the acceptable response as set by the user 48, the user 48 is also alerted. In another non-limiting embodiment, in the event that the result of the task falls outside the acceptable response as set by the user 48, a first responder 52 and/or member of the patient's support group 56 is alerted. The alert can be by way of a telephone call, sms message, and/or a visual and/or auditory tone. The user electronic device 45 may also receive data automatically through the user interface 44 from a preprogrammed application existing on the user electronic device 45 and may be based on, for example information stored in the one or more database(s) 16 or the data received from the patient 46.

In some embodiments, the patient electronic device 43 allows for live audio and video calling between the patient 46 and the user 48. During calls, the user interface 44 that is used by the user 48 may include an augmented user interface 58 which allows the user 48 to experience an augmented version of the call while keeping the patient 46 in clear view and without pausing the call or video. The augmented user interface 58 may include a patient viewing window 76 showing a video representation of the patient 46 and a user viewing window 78 showing a video representation of the user 48, which windows 76, 78 can be positioned in various ways relative to one another (e.g., the sizes of the windows 76, 78 can be adjusted, the windows 76, 78 can be moved, and/or the orientation of the windows 76, 78 can be changed). For example, the augmented user interface 58 may be a picture-in-picture window, with at least one smaller window within a larger, full-screen window. In certain non-limiting embodiments, the larger window may be the patient viewing window 76 and the at least one smaller window may be the user viewing window 78. Other smaller windows of the augmented user interface 58 may include one or more overlay user interface screen(s) 80 overlaying the patient viewing window 46 and/or user viewing window 48. The overlay user interface screen(s) 80 may be partially or fully translucent so as to not decrease visualization of either the patient viewing window 76 or the user viewing window 78. The overlay user interface screen(s) 80 and windows 76, 78 can be positioned in various ways relative to one another (e.g., the sizes of the windows 76, 78 can be adjusted, the windows 76, 78 can be moved, and/or the orientation of the windows 76, 78 can be changed). For example, FIGS. 5A-5D show the augmented user interface 58 with a patient viewing window 76, user viewing window 78, and overlay user interface screen(s) 80 when a video call is in session.

Figure 5A:
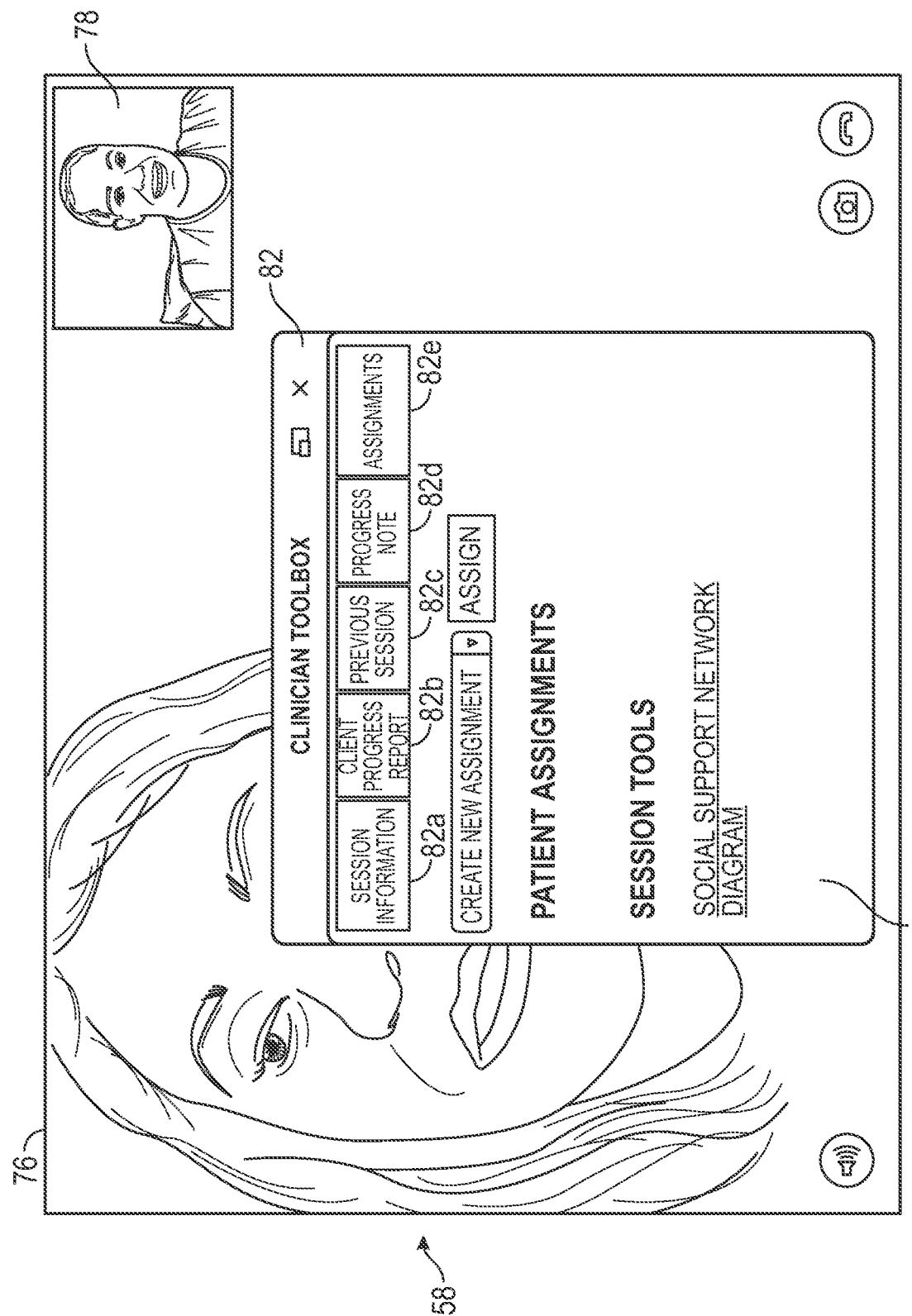
FIG. 5A-D illustrate screen shots of an example user interface with graphical user interface screens thereon when a video conference session is active.
Figure 5B:
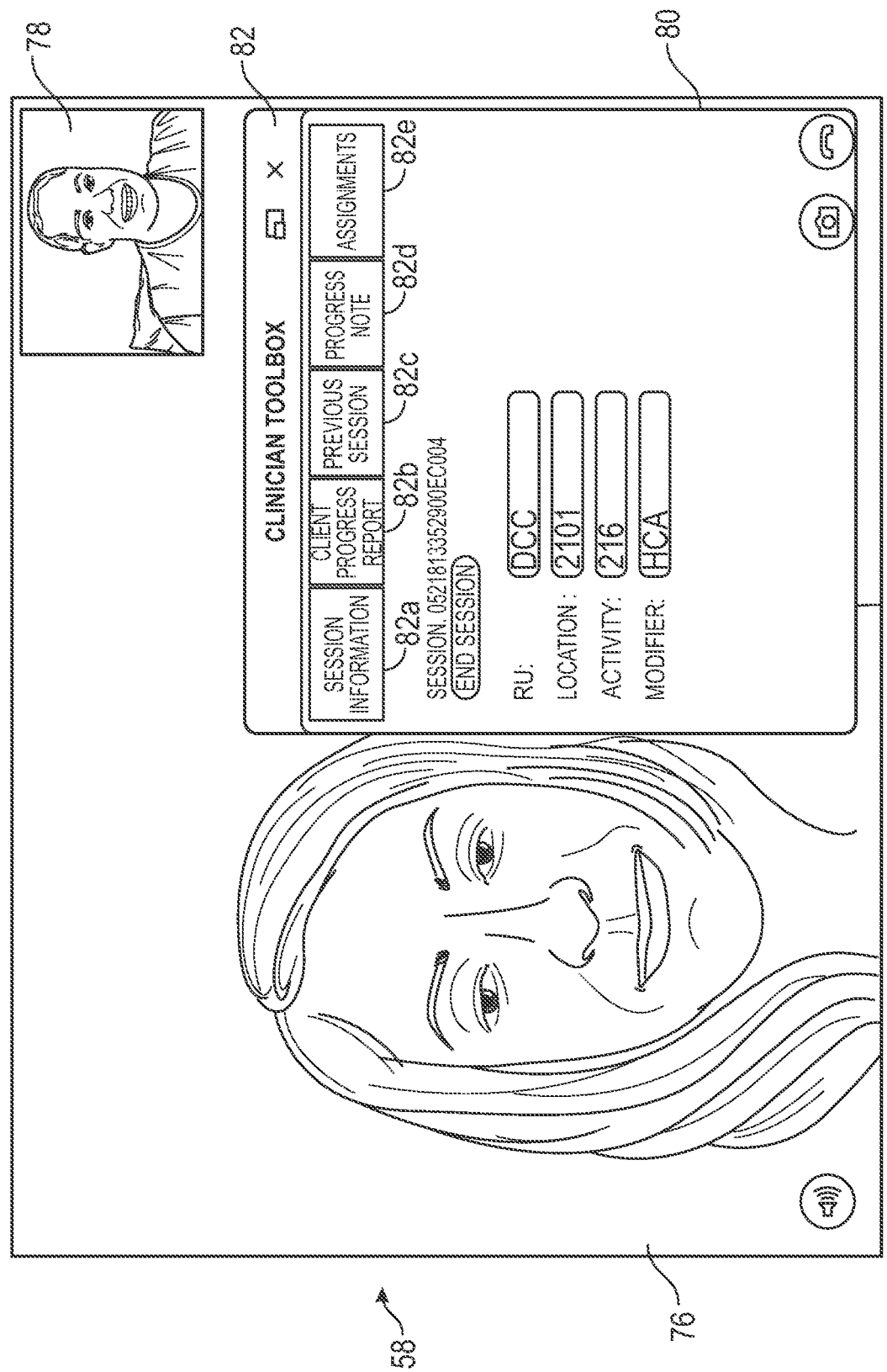
Figure 5C:
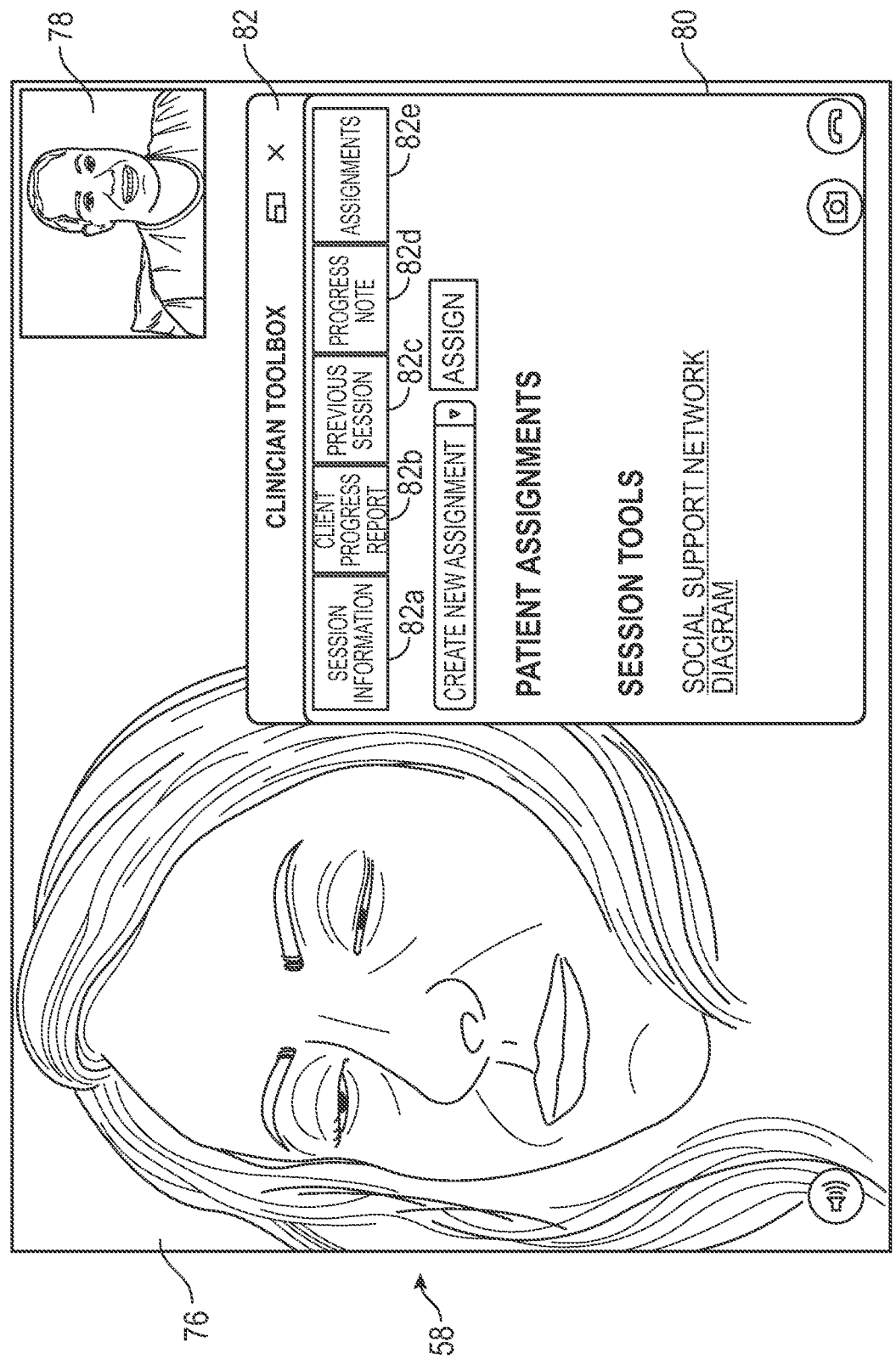
Figure 5D:
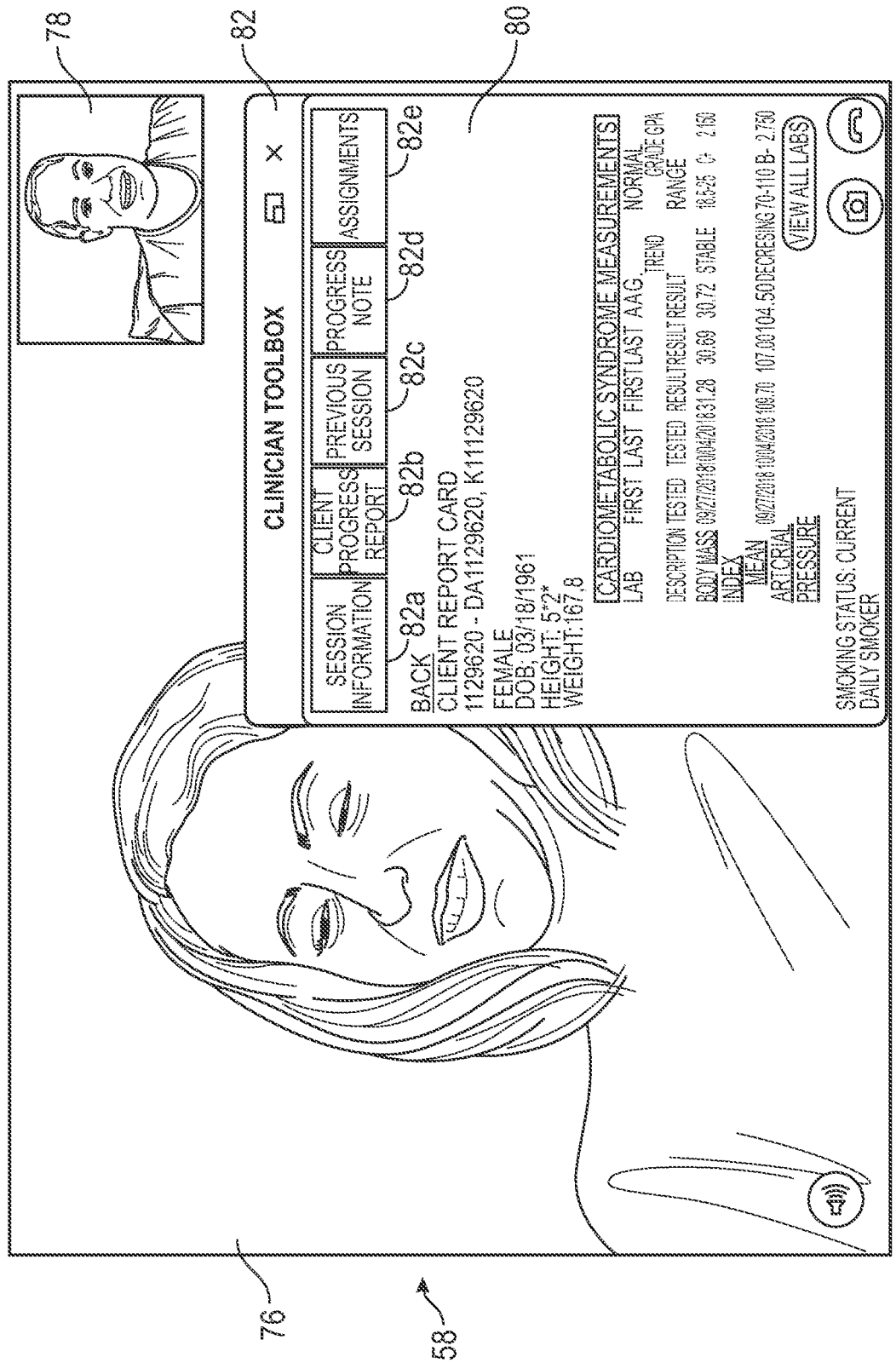

In traditional video systems, when two parties are using different aspect ratios from one another (i.e., one in portrait and one in landscape), the resulting video image (or the patient viewing window 76 or the user viewing window 78) is always centered. In some embodiments, when two parties are using different aspect ratios from one another, in the patient interface 42 the user viewing window 78 remains centered but in the user interface 44, the patient viewing window 76 can automatically move to the center, left, right, top, or bottom, depending on whether the user 48 has augmented content displayed. For example, FIG. 5B shows that when the patient 46 moves her patient electronic device 43 into portrait mode, the patient viewing window 46 in the user interface 44 automatically shifts to the left, allowing for maximum utilization of the screen space. In some embodiments, when in a non-matched aspect ratio, the user 48 can move the patient viewing window 46 to the center, left, right, top, or bottom. In some embodiments, when two parties are using different aspect ratios from one another, in the user interface 44 the patient viewing window 76 remains centered but in the patient interface 42, the user viewing window 78 can automatically move to the center, left, right, top, or bottom.

In certain non-limiting embodiments, the overlay user interface screen(s) 80 may include a user menu 82 which includes session options 83a, 83b, 83c, 83d, and 83e, referred to generally as "session options 83" being configured to allow the user 48 to enter information into the overlay user interface screen 80 and thereby document calls with the patient 46 in real-time. The user menu 82 may include a "session information" option 83a, "client progress report" option 83b, "previous session" option 83c, "progress note" option 83d, "assignments" option 83e, and/or other session options 83 (e.g., "client behavior," "problem/objective," "services discussed," "finalize session," "patient signature," or other options) that allow the user 48 to quickly and easily document calls with a patient 46 in real-time. The user menu 82 and session options 83 therein are configured to allow the user 48 to document a session record 84 during a session with patient 46. Each session option 83 may be selected, which opens the session option 83 in an overlay user interface screen 80 and then information can be entered into that overlay user interface screen 80. Information entered into the overlay user interface screen 80 is transmitted to the application server 12 and stored in the memory 18 as an update to a patient electronic health record (also referred to as a patient electronic medical record or "EMR") for the patient 46.

Each session option 83 may also include various means of entering data such as text boxes, check boxes, slider controls, multiple choice options, automatically-generated suggestions, and other forms of displaying information or inputting data to assist the user 48 during the video call. The entered data may be automatically compiled in a session record 84 that is kept for each session. For example, the entered information may be added to a session record 84 in complete sentence format to provide quick record-keeping capabilities that only requires the user 48 to review for error before the session record 84 is stored in the remote healthcare system 10. Additionally, the session record 84 may be shared with the patient 46 during a call, as further discussed below.

Figure 7:
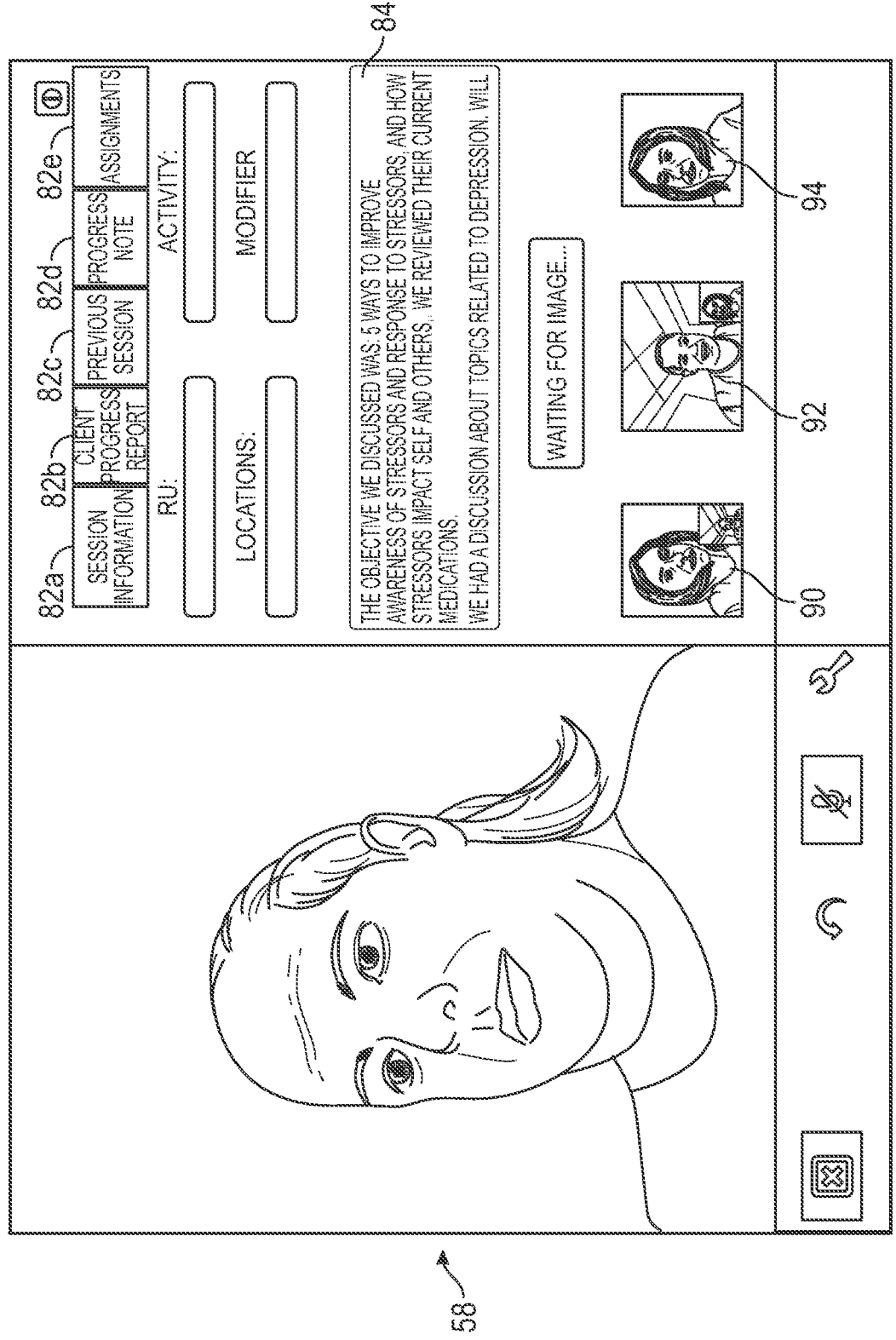
FIG. 7 illustrates a screen shot of another example user interface with graphical user interface screens thereon following a video conference session.

A user 48 may end a video session, for example, by selecting the "patient signature" or "finalize session" option. When the "patient signature" option is selected by a user 48, the option may visually change on the augmented user interface 58 (e.g., to read "waiting," "waiting for image," or the like) to convey that the request is in progress. As shown in FIG. 7, the augmented user interface 58 also displays the session record 84 (and still images as further discussed below with respect to the Session Documenter feature) for the user's review. A patient's signature may be required at the end of a session and may be encrypted and stored along with the session record 84 from that call.

The picture-in-picture design of the augmented user interface 58 has many advantages over traditional voice calls or video calls such as, allowing the user 48 to perform various activities without breaking eye contact with the patient 46, such activities including, but not limited to, entering information into the electronic device 45 to keep records of therapy sessions, sending information, or assigning tasks; accessing patient information from the database 16 such as past assessment results, previous session data, medication listings, and lab results; and reading information from the database 16 or information provided by patient 46.

Figure 6A:
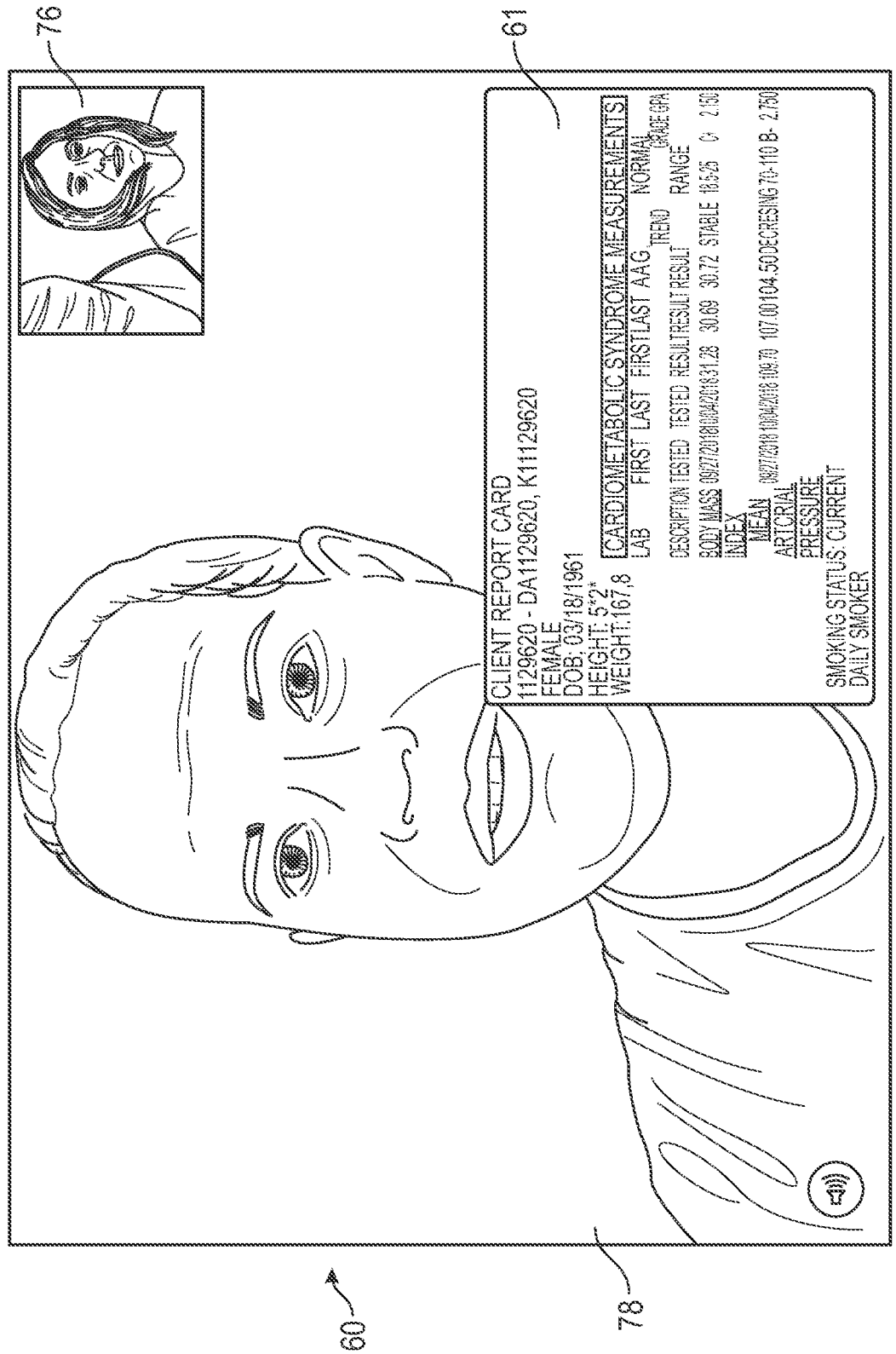
FIGS. 6A and 6B illustrate screen shots of another example patient interface with graphical user interface screens thereon when a video conference session is active.

The augmented user interface 58 also allows the user 48 to "share" any information being viewed by the user 48 with the patient 46, who is able to view "shared" information on an augmented patient interface 60 on the patient interface 42. The patient electronic device 43 receives data from the user 48 through the patient interface 42 regarding the patient's health information and care, which data is transmitted to the application server 12 and stored in the memory 18. For example, the application server and system processor 12 are coupled to the memory 18, which stores instructions that, when executed by the system processor 12, cause the application server and system processor 12 to receive an instruction from the user electronic device 45, and then present on the augmented patient interface 58, in a read-only format (as shown in FIG. 6A), at least a portion of the information entered into an overlay user interface screen 80.

Figure 6B:
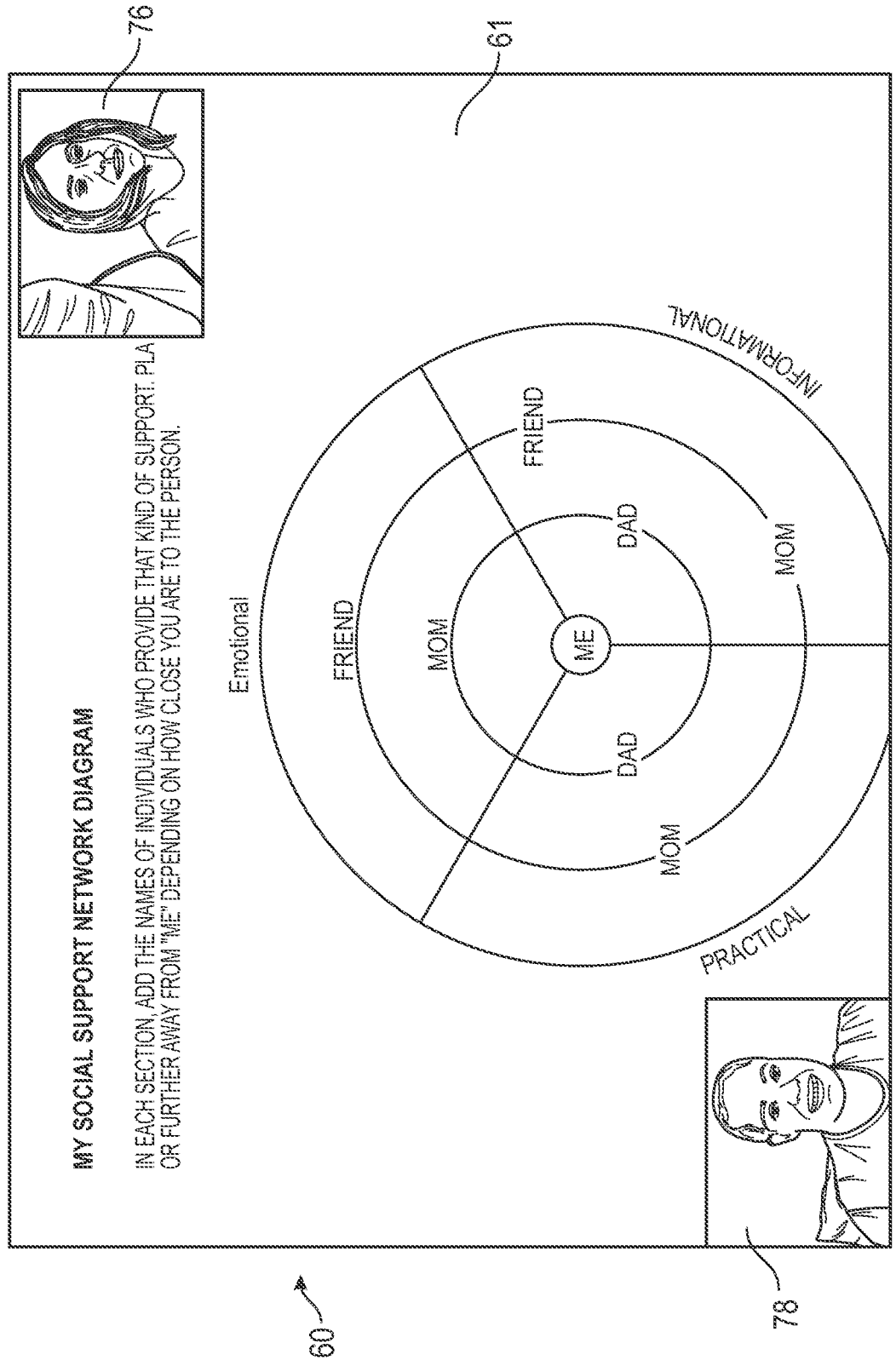

During calls, the patient interface 42 that is used by the patient 46 may include an augmented patient interface 60. The augmented patient interface 60 may include a patient viewing window 76 showing a video representation of the patient 46 and a user viewing window 78 showing a video representation of the user 48, which windows 76, 78 can be positioned in various ways relative to one another (e.g., the sizes of the windows 76, 78 can be adjusted, the windows 76, 78 can be moved, and/or the orientation of the windows 76, 78 can be changed). For example, the augmented patient interface 60 may be a picture-in-picture window, with at least one smaller window within a larger, full-screen window. In certain non-limiting embodiments, the larger window may be the user viewing window 78 and the at least one smaller window may be the patient viewing window 76. Other smaller windows of the augmented patient interface 60 may include one or more overlay patient interface screen(s) 61. The overlay patient interface screen(s) 61 may be partially or fully translucent so as to not decrease visualization of either the patient viewing window 76 or the user viewing window 78. The overlay patient interface screen(s) 61 and windows 76, 78 can be positioned in various ways relative to one another (e.g., the sizes of the windows 76, 78 can be adjusted, the windows 76, 78 can be moved, and/or the orientation of the windows 76, 78 can be changed). For example, FIGS. 6A and 6B show the augmented patient interface 60 with a patient viewing window 76, user viewing window 78, and overlay patient interface screen(s) 61 when a video call is in session. FIG. 6B shows the overlay patient interface screen as a full screen display, with windows 76, 78 as thumbnail windows.

In certain non-limiting embodiments, the overlay patient interface screen(s) 61 may include a window displaying any "shared" information that was shared by the user 48, such as a progress note, or a window displaying the session record 84 and requesting the patient's signature at the end of a session.

During video calls, the system interface 14 includes a feature that automatically takes screenshots at timed intervals throughout the video call. This feature may be referred to as the "Session Documenter" and captures and stores still images of the audio-video session, the still images including the patient viewing window 76 and the user viewing window 78. In some embodiments, the Session Documenter captures and stores still images of the audio-video session, the still images including the patient viewing window 76 and the user viewing window 78 and excluding the overlay user interface screen(s) 80. The Session Documenter may be configured to capture and store the still images at an interval. For example, the Session Documenter captures and stores a first still image 90 at a first instance of time upon initiation of the audio-video session (such as, as soon as both the patient 46 and user 48 have entered the session), and a second still image at a second instance of time upon ending the audio-video session, and wherein the Session Documenter presents the first still image and the second still image 94 on the augmented patient interface 60 with a prompt for the patient 46 to sign thereby authorizing the application server and the system processor 12 to store the first still image 90 and the second still image 94 as part of the patient's electronic health record.

The Session Documenter can also be customized to capture and store at least one third still image 92 at a third instance of time, the third instance of time being between the first instance of time and the second instance of time, the third still image 92 being stored with the patient's electronic health record. The third still image 92 may be taken at predetermined intervals throughout the video session. By way of example, the Session Documenter can capture and store at least one third still image 92 every 1 minute, or every 2 minutes, or every 3 minutes, or every 4 minutes, or every 5 minutes, or at a time greater than 5 minutes, until the end of the audio-video session. The Session Documenter can take still images at equal intervals or at varying intervals.

A user 48 may end a video session, for example, by selecting the "patient signature" or "finalize session" option, which also triggers the taking of the second still image 94 at the end of the video session. At the end of a session, a predetermined number of still images, such as three, may be stored with the session record 84. For example, the session record 84 can be stored with the first still image 90, second still image 94, and at least one third still image 92 that is randomly selected by the Session Documenter.

When the "patient signature" option is selected by a user 48, the patient 46 receives a request on the augmented patient interface 60 for the patient's signature. The Session Documenter displays a prompt requesting the patient's signature attached to the selected still images 90, 92, 94 and the session record 84 for the patient's review via the augmented patient interface 60. As shown in FIG. 7, the augmented user interface 58 also shows that the patient's signature was requested along with the selected still images 90, 92, 94 and the session record 84 for the user's review. In other embodiments, the augmented patient interface 60 and augmented user interface 58 each displays only the request for patient signature attached to the selected still images 90, 92, 94 for the patient's and user's review. The patient's signature authorizes the application server and the system processor 12 to store the selected still images 90, 92, 94 as part of the patient's electronic health record. Once signed, the patient's signature is encrypted and stored along with the selected still images 90, 92, 94 and session record 84 from that call as part of the patient's electronic health record.

All of the still images taken and stored by the Session Documenter are encrypted and are not editable—even those that were not used as a selected still image for the patient's and user's review. The Session Documenter is configured to embed an encryption key into the still images specific to the live audio-video session. In some embodiments, the patient's signature embeds an encryption key into the still images specific to the live audio-video session.

The request for patient's signature and patient's signature (attached to selected still images 90, 92, 94 and session record 84) may stay on the server such that certain information, such as the length of call and participants, is stored on the server. Conversely, the video itself may be a point-to-point connection that does not hit the server.

In the event that a video session is disconnected without being finalized (i.e., by the user 48 selecting the "patient signature" or "finalize session" option), the session can be resumed such that the Session Documenter retains the first still image 90 and continues collecting still images as though the session had never ended.

The Session Documenter feature has many advantages over traditional video calls such as, securely storing comprehensive documentation for the use of various parties such as auditors, users, users' employers, patients, and patients' guardians. The still images can be used to provide proof of a session's occurrence and proof of the propriety of sessions, which may be requested in, for example, video sessions with unaccompanied minors. Still images that are stored but were not used as a selected still image are available for future reference if they are ever needed. For example, algorithms can be run against the stored still images to screen for poor video quality or for inappropriate conduct. Additionally, the videos being point-to-point connection provides an additional security benefit for a user and user's employer, such as hospitals.

Figure 8:
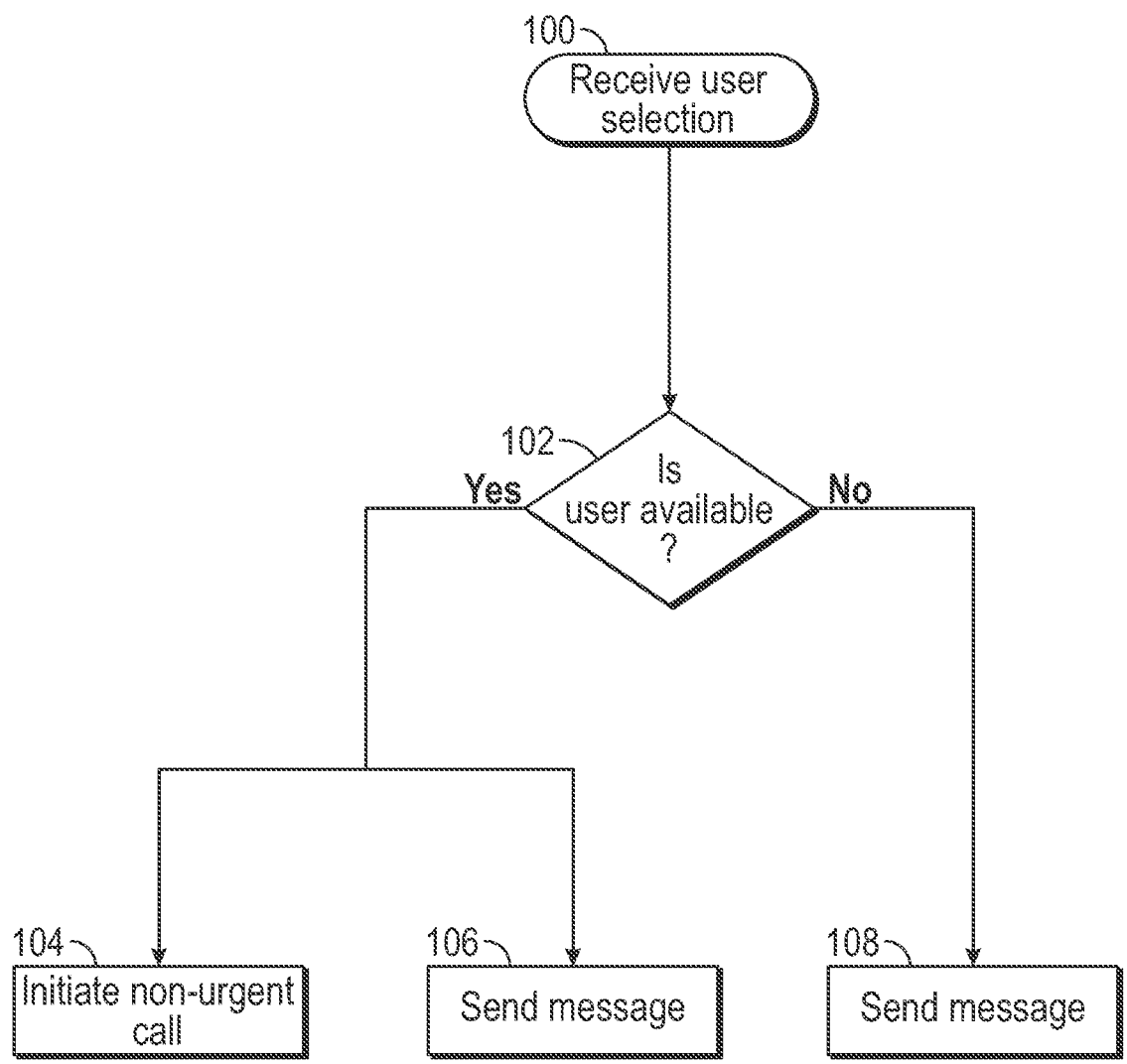
FIG. 8 is an exemplary function flow chart of a method for a patient to contact a user within the patient interface in a non-emergency situation.

The patient electronic device 43 also allows for emergency and non-emergency calls from the patient 46 to the user 48. FIG. 8 depicts a flow chart of an exemplary method for a patient 46 to contact a user 48 within the patient interface 42 in a non-emergency situation. As shown in FIG. 8, in a non-emergency situation, the patient electronic device 43 receives a user selection identifying the user 48 (step 100). Then, the application running on the patient electronic device 43 checks the user's 48 availability (step 102). If the user 48 is not available, the application running on the patient electronic device 43 sends a message (SMS, email, or the like) to the user 48 informing the user 48 that the patient 46 would like to communicate with the user 48 (step 108). If the user 48 is available, the application running on the patient electronic device 43 either initiates a non-urgent telephone/video call with the user 48, or sends a message to the user 48 to inform the user 48 that the patient would like to communicate with the user 48 (steps 104 and 106). Steps 100 and 102 are also illustrated in FIG. 3C, which depicts a patient interface 42 with a user selection identifying users 48 and their availability, which can be indicated by color-coding so that the availability of a user 48 can be immediately recognizable by the patient 46. For example, an available user may have a green filled-in circle near his name and an unavailable user may have red filled-in circle near his name.

Figure 9A:
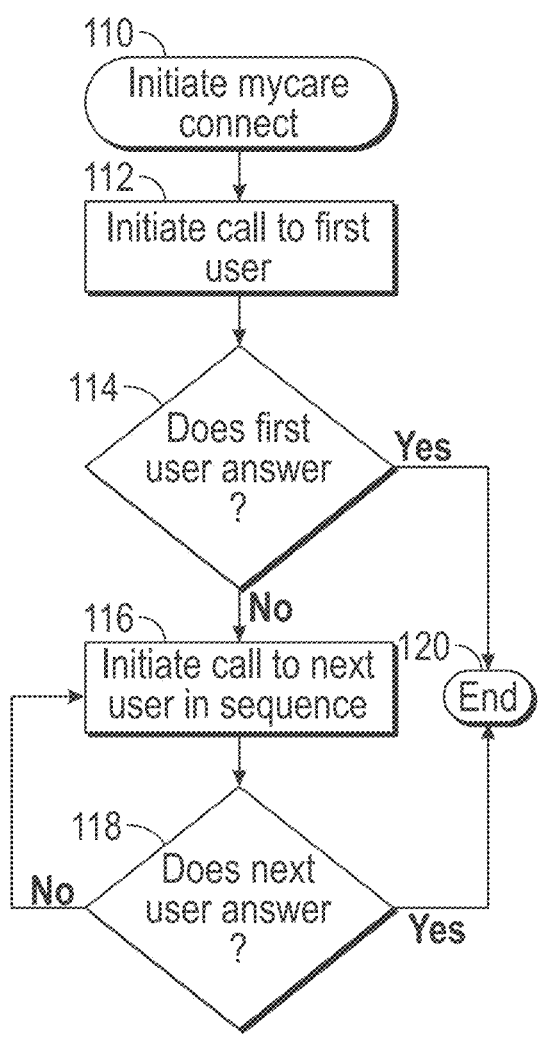
FIG. 9A is a block diagram illustrating example navigation of a patient within the patient interface for the purposes of placing a crisis call.
Figure 9B:
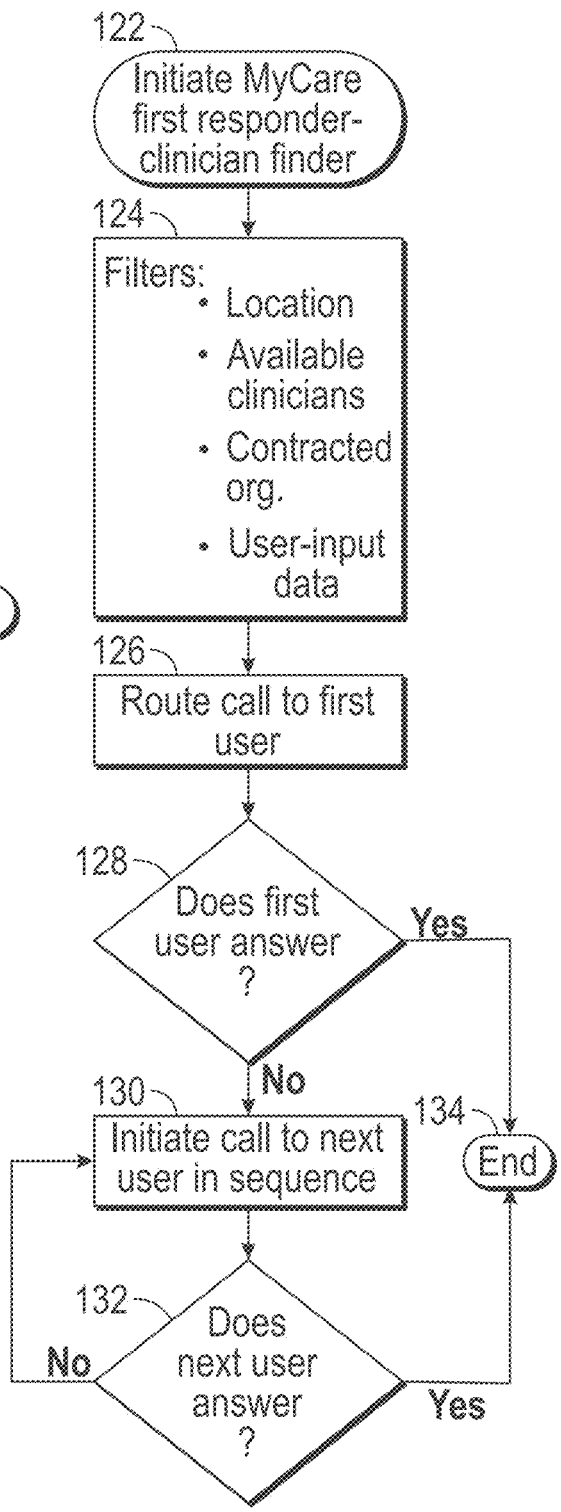
FIG. 9B is a block diagram illustrating example navigation of a patient within the patient interface for purposes of a data-triggered crisis call.

FIGS. 9A and 9B depict flow charts of exemplary methods for placing a crisis call in an emergency situation. As illustrated in FIGS. 9A and 9B, a crisis call may be initiated by several ways: a patient 46 may manually select the crisis button 62 on the patient interface 42 of the patient electronic device 43; the crisis call may be automatically triggered by data input and/or results detected by the patient electronic device 43; or the user may 48 may manually select a crisis mechanism such as a crisis button (not pictured). The crisis button 62 may be visible to the patient 46 on the patient interface 42. In one non-limiting embodiment, the crisis button 62 may be visible to the patient 46 no matter what screen the patient 46 is on within the patient interface 42. FIGS. 9A and 9B depict crisis call protocols for contacting a user 48, however, the protocols in FIGS. 9A and 9B can also be used for contacting first responders 52 and the patient's support group 56. In certain non-limiting embodiments, when the crisis button 62 is selected, the protocols for contacting users 48, first responders 52, and the patient's support group 56 are automatically and simultaneously initiated.

The system interface 14 may also include a first responder electronic device 51 comprising the first responder interface 50 that is accessed by a first responder 52. When a crisis call is initiated (either manually or automatically), the patient's location may be sent to one or more first responder 52. The first responder device 51 receives data, such as the patient's location, through the first responder interface 50, which data is transmitted to the application server 12 and stored in the memory 18. As discussed in further detail below, the memory 18 also stores one or more database 16 containing information indicative of electronic contact information for at least one first responder 52 associated with the patient 46. The patient electronic device 43 includes a device locator determining real-time location of the patient electronic device 43, and wherein the at least one of the patient interface 42 or the user interface 44 includes (or the patient electronic device 43 automatically triggers) a crisis mechanism including instructions that cause the system processor 12 to read the real-time location of the patient electronic device 43, read electronic contact information for the at least one first responder 52, and send a crisis message to the first responder device 51 including an identity of the patient 46, and the real-time location of the patient electronic device 43. The patient's location can be determined using Global Positioning System (GPS) tracking on the patient electronic device 43, address information stored on the patient electronic device, or address information input by the patient 46, or other ways of determining the patient's location.

System Processor and Application Server 12

The system processor and application server 12 retrieves and executes instructions stored in the memory 18 to control the operation of the remote healthcare communication system 10. Any number and type of conventional computer, computer system, computer network, computer workstation, minicomputer, mainframe computer, or computer processor, such as an integrated circuit microprocessor or microcontroller can be used in conjunction with the present invention. As those skilled in the art will appreciate, any computer used in accordance with aspects of the present invention may include an operating system (e.g., Windows NT, 95/98/2000/XP/Vista, OS2, UNIX, Linux, Solaris, MacOS, etc.) as well as various conventional support software and drivers typically associated with computers. In certain non-limiting embodiments, dedicated electronic device applications may be entirely or partially served or executed by the system processor 12 in performing methods or processes of the presently claimed inventive concepts.

Memory 18

The exemplary system in FIG. 2 includes a memory 18. The system processor and application server 12 retrieves and executes data stored in the memory 18, such as data stored in one or more database(s) 16 stored in the memory 18. Generally, the memory 18 stores one or more database(s) 16 containing information forming a patient electronic health record for the patient. The memory 18 stores instructions, patient information, patient conditions, patient medical history, and any other suitable information. A memory operating in conjunction with the presently claimed inventive concepts may include any combination of different memory storage devices, such as hard drives, random access memory (RAM), read only memory (ROM), FLASH memory, or any other type of volatile and/or nonvolatile memory. Systems and methods for remote patient monitoring may also store and retrieve data from one or more database(s) 16 stored in the memory 18 that may be chosen from, for example but not by way of limitation, Patient Information Repository 20, Connect 22, Behavioral Information Repository 24, Billing 26, Biometric Information Repository 28, Knowledge Base 30, Biological Information Repository 32, Rules Database 34, Pharmacy Records 36, Health Information Exchange (HIE) Information 38, and Laboratory and Repository 40 depicted in FIG. 2. In one embodiment, this data is generated by one or more medical devices and transmitted to the application server 12. In another non-limiting embodiment, the data is input by a user 48 and/or by a patient 46 and transmitted to the application server 12.

The patient information repository 20 may include patient identification information such as name, address, and electronic health or medical record. The electronic health record generally refers to a digital version of all of the information that is typically found in a provider's paper chart, for example but not by way of limitation, medical history, diagnoses, medications, immunization dates, allergies, lab results and doctor's notes. The patient information repository 20 may also include a patient's program enrollment. For example, when a new patient (such as patient 46) is entered into the remote healthcare communication system 10, the patient may be enrolled in a specific program based on the patient's mental health level—i.e., highly depressed, slightly depressed, etc. The patient information repository 20 may also be used to store medical data from any suitable source, such as from one or more medical devices used by a patient. The patient information repository 20 may include data for individual patients (and identified as such) or general data from groups of patients. Such information can be used to diagnose trends in a population of patients or identify a condition for a patient exhibiting particular symptoms.

Connect 22 allows for the storage and retrieval of electronic contact information for a patient's support group having at least one support group member, or at least two support group members. Exemplary electronic contact information includes telephone number(s), email address, and the like. In certain embodiments, a user 48 and/or patient 46 may register and associate members of a patient's support group (such as a parent, legal guardian, family member, friend, or other person selected by the patient 46) to that patient 46, which allows for the user 48 and/or patient 46 to electronically contact the members. These members may be referred to as "Connect members." A user 48 and/or patient 46 may also select and store parameters for the Connect members, such as which Connect members are allowed to be called during a specified day(s) and/or time(s), or designate a hierarchy of the Connect members, which would specify which Connect member(s) is the patient's parent(s) or legal guardian(s) and instruct the order in which Connect member(s) should be contacted, for example, in cases of emergency. Connect 22 may also comprise instructions that, when executed by the system processor 12, cause the application server and system processor 12 to: establish a live audio session between the user 48 and at least one of the support group members using the electronic contact information stored in the Connect 22 database. When Connect 22 comprises instructions designating a hierarchy of the Connect members, and further comprising instructions that, when executed by the system processor, cause the application server and system processor 12 to: establish a live audio session between the user 48 and at least one of the support group members using the electronic contact information and the hierarchy stored in the Connect 22 database.

In another non-limiting embodiment, one or more Connect member(s) are able to call the patient 46 but cannot be called by the patient 46. In another non-limiting embodiment, one or more Connect member(s) may receive calls from a user 48, but not a patient 46. Once the Connect members are stored in Connect 22, a patient 46 may initiate a three-way call with a user 48 and a Connect member. In one non-limiting embodiment, a patient 46 may be flagged (e.g., manually by the user 48 or automatically by the system 10) such that the patient 46 or user 48 must initiate a three-way call that includes a Connect member before a call or session can be started with that patient 46. For example, the user 48 may flag a minor or legally incompetent patient who requires a parent or legal guardian to be present in order to conduct a telemedicine session.

Connect 22 may also include a feature that allows a user to conduct sessions with a flagged patient without a parent or legal guardian also being present on the voice call or video call. Connect 22 in memory 18 stores a flag for such a flagged patient. This feature may be referred to as "Session Guardian" and can be used if the flagged patient's parent or legal guardian (i.e., "session guardians") has given prior consent.

In some embodiments, the Session Guardian feature comprises instructions that, when executed by the system processor, cause the application server and system processor 12 to establish a three-way call with the flagged patient, the user, and the session guardian prior to establishing the live audio-video session between the user and the flagged patient.

In other non-limiting embodiments, Connect 22 in memory 18 stores a flag for the patient indicating that the user is allowed to conduct sessions with the patient without a parent or legal guardian being present, and wherein the instructions that, when executed by the system processor, cause the application server and system processor to: read the flag stored in the memory and then establish the live audio-video session between the user and the patient without the presence of the parent or legal guardian.

Prior to starting a session with a flagged patient, the Session Guardian feature comprises instructions that, when executed by the system processor, cause the application server and system processor 12 to automatically send, or the user manually send, a message (SMS, email, or the like) to one or more of the flagged patient's session guardian(s), requesting permission for the user to begin the session with the flagged patient. The Session Guardian feature will not allow a session to begin until a session guardian responds affirmatively. The message may be sent at any time within a day before the session, such as 24 hours prior to the session, or 20 hours prior to the session, or 15 hours prior to the session, or 10 hours prior to the session, or 5 hours prior to the session, or 1 hour prior to the session, or immediately prior to the session. If an affirmative response is not received prior to a predetermined amount of time prior to the session, the Session Guardian feature can automatically send a follow-up message to one or more of the flagged patient's parent(s) or legal guardian(s), and/or text an alternative parent or legal guardian, based on the designations made in Connect. If an affirmative response is not received, the Session Guardian feature automatically cancels the session and sends a message to the flagged patient's parent(s) or legal guardian(s). Responses, or the lack thereof, are sent to the user interface 44 and may be color-coded so that the status of a session can be immediately recognizable by the user 48. For example, an affirmative response may be green, a negative response may be red, and no response may be grey. The Session Guardian feature may be removed, for example, when a minor patient turns 18 years old or when a legally incompetent patient is determined to be competent.

In some embodiments, the Session Guardian feature comprises instructions that, when executed by the system processor, cause the application server and system processor 12 to establish a three-way call with the flagged patient, the user, and the session guardian prior to establishing the live audio-video session between the user and the flagged patient.

In some embodiments, secondary verification may be required from the flagged patient's session guardian to confirm that it is indeed the flagged patient's session guardian. For example, secondary verification may include a picture, password, or the like.

In some embodiments, the Session Guardian feature also alerts the flagged patient that a message has been sent to the flagged patient's session guardian. The flagged patient may be notified for various reasons, such as, the request has been sent, the request has been accepted, the request has not been accepted, or the like.

The behavioral information repository 24 allows for the storage and retrieval of a patient's behavioral data. Behavioral data may be an aggregation of data captured from one or more of: a patient through a variety of mechanisms (patient homework assignments, journals, messages, and the like), patient information input by the user 48, and patient records stored in the memory 18. After its collection, behavioral data is transmitted to the application server 12, and stored in the repository 24. In certain non-limiting embodiments, the behavioral information is available to users 48 through the system interface 14.

Figure 10:
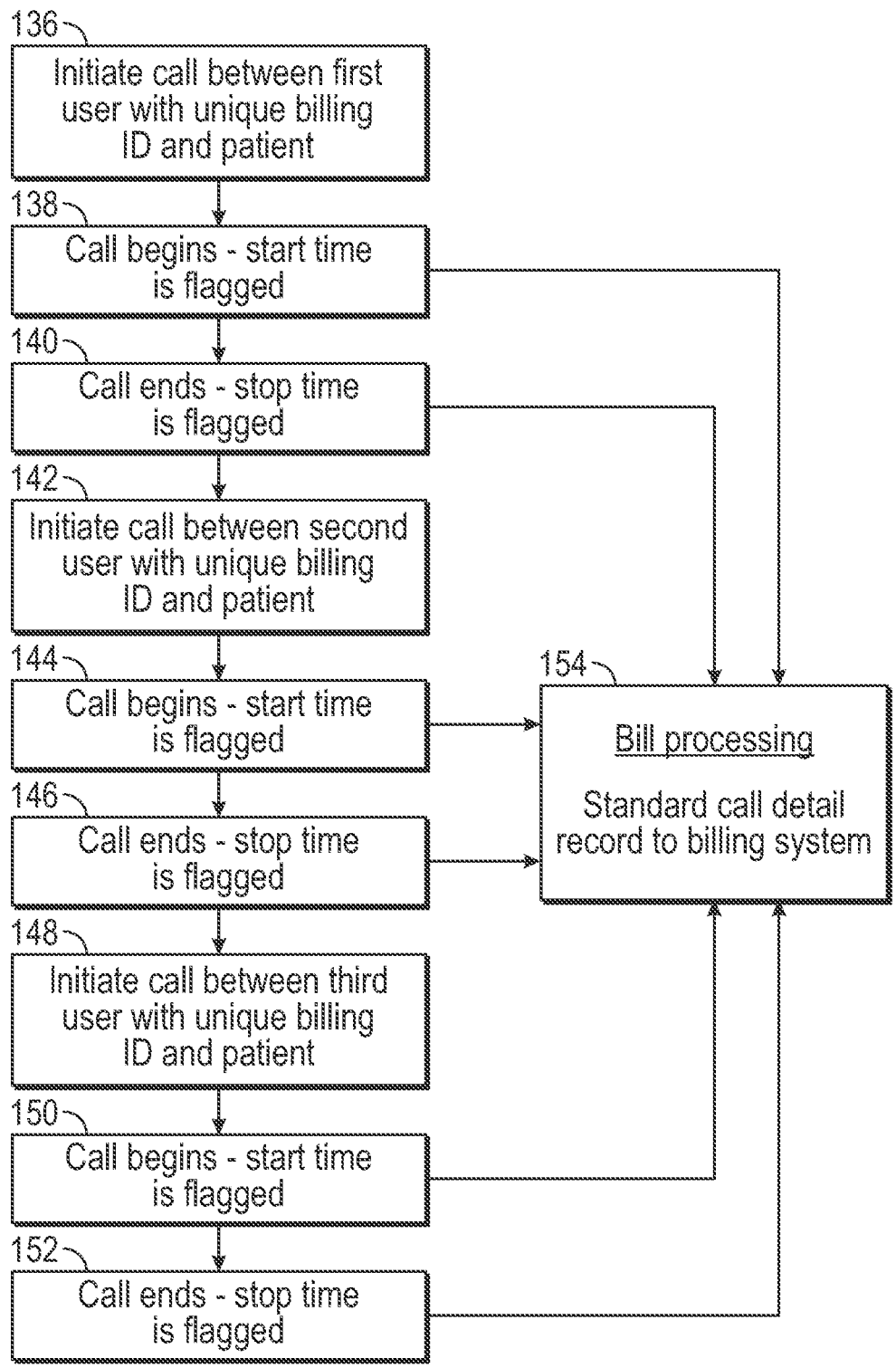
FIG. 10 is a block diagram illustrating an example of automatic call handoff billing.
Figure 11:
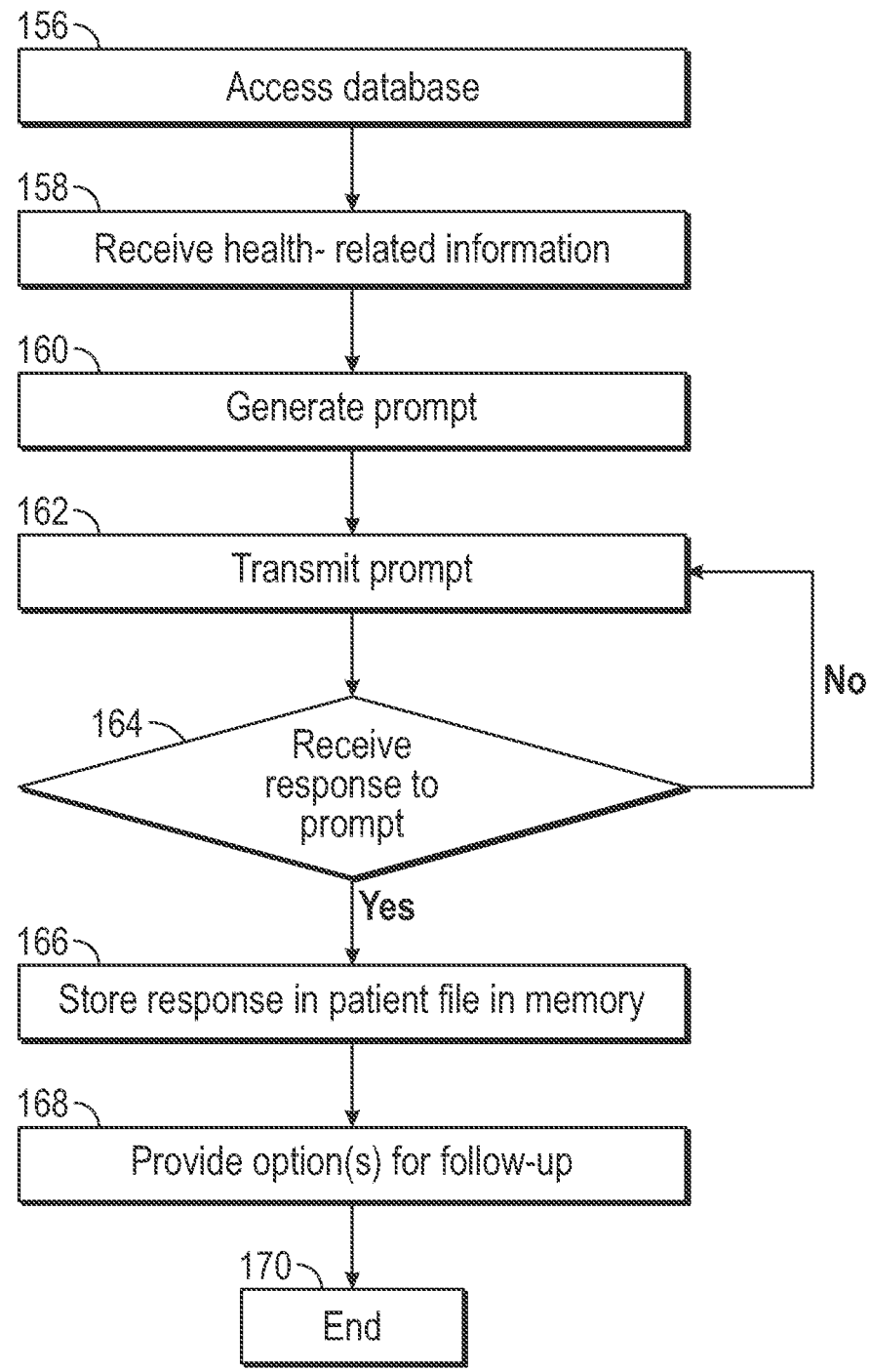
FIG. 11 is a block diagram showing a routine that illustrates an aspect of automatic health monitoring and tracking method in accordance with one or more embodiments
Figure 12:
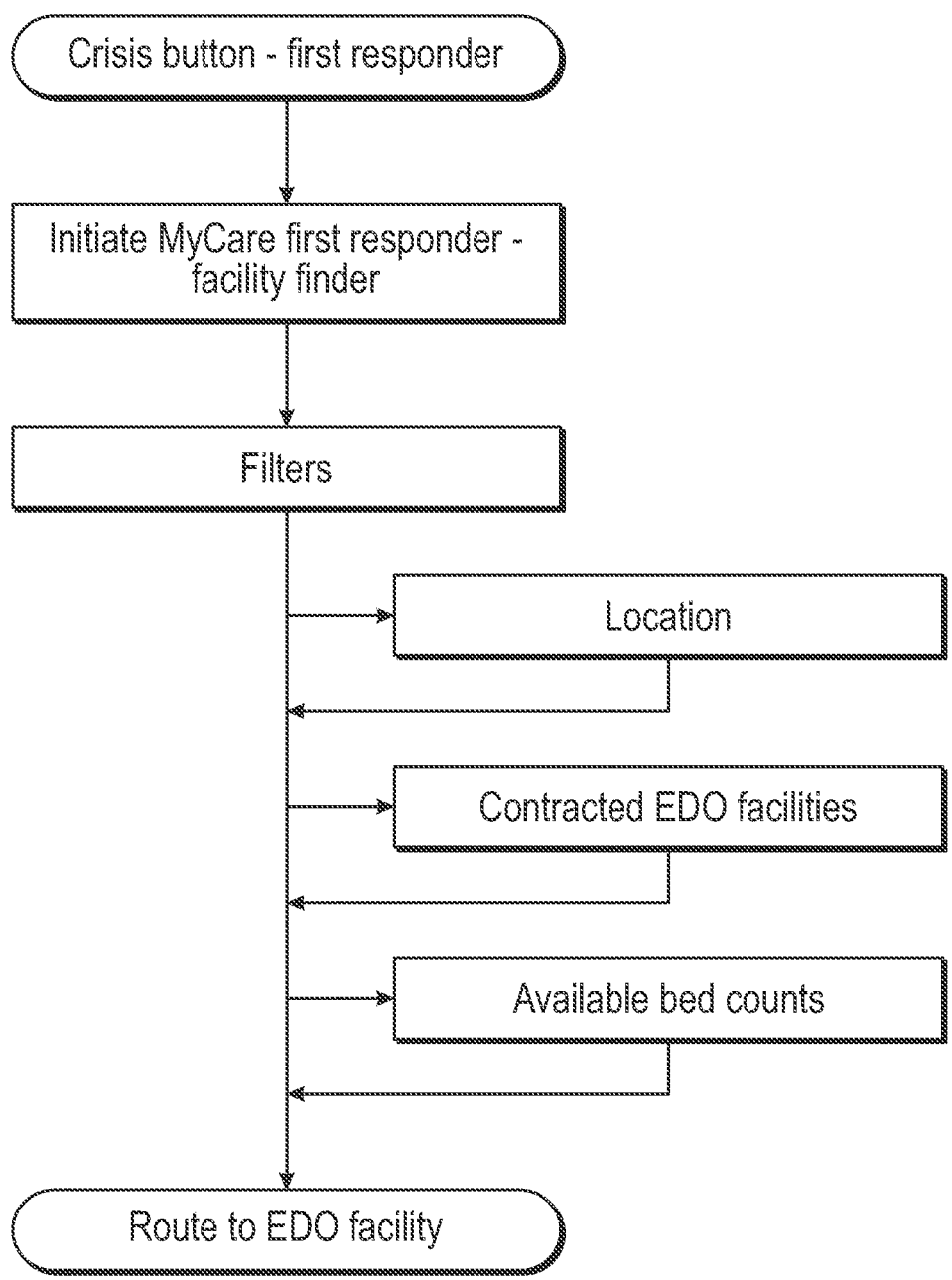
FIG. 12 is a block diagram illustrating an exemplary navigation of a first responder within the first responder interface for the purposes of placing a crisis call to find an Emergency Detention Order ("EDO") facility.

The billing repository 26 allows for the storage and retrieval of billing information such as the billing rate(s) for one or more user(s) 48, previous bills, outstanding bills, and the like. The billing repository 26 allows for this information to be accessed by the server 12, which then utilizes this information to create billing lines. For example, when an audio-video session begins, the start time is flagged by the server 12 by saving an entry indicative of the start time in the billing repository 26. When the session ends, the end time is flagged by the server 12 by saving an entry indicative of the end time in the billing repository 26. The server 12 then utilizes this information to create an appropriate billing line and billing duration based on the length of the session. In the event that more than one user 48 is needed during a session, the initiating user can generate a three-way video session to create a warm handoff to a second user. For example, as illustrated in FIG. 10, the initiating user is a first user 48a, and the live audio-video session is a first audio-video session of a treatment session for the patient 46 (steps 138 and 140). The billing repository 26 comprises instructions that, when executed by the system processor, cause the application server and system processor 12 to: end the first audio-video session of the treatment session for the patient 46, and establish a second live audio-video session between the patient 46 and a second user 48b as part of the treatment session for the patient 46, the first and second live audio-video sessions being substantially contiguous (steps 142, 144, and 146). The server 12 automatically generates appropriate billing lines for both users 48 without overlapping (double-billing) for any user 48 (step 156).

The billing repository 26 stored in memory 18 may also store billing rates for users 48 and rules that allow the server 12 to automatically select the most appropriate billable user 48 for any or the entire shared portion of the session. More specifically, the billing repository 26 may store a first billing rate for the first user 48a, and a second billing rate for the second user 48b, wherein a first audio-video session encompasses a first time period stored in the billing repository 26, and a second audio-video session encompasses a second time period stored in the billing repository 26, and wherein the instructions in the billing repository 26 further issue an invoice including the first billing rate and the first period of time, and the second billing rate and the second period of time. For example, if a first user 48a initiates the hand-off and his session is billable in 15-minute increments, the server 12 will automatically change over the billing line to the second user 48b once the session has reached 16 minutes.

The biometric information repository 28 allows for the storage and retrieval of a patient's and/or user's biometric data. In certain embodiments, biometric data is captured from a patient 46 through the patient interface 42, transmitted to the application server 12, and stored in the repository 28. In another non-limiting embodiment, biometric data is captured from the user 48 through the user interface 44, transmitted to the application server 12, and stored in the repository 28. In certain embodiments, biometric measurement captured from the patient 46 and/or user 48 may be rendered into digital representations.

The knowledge base 30 is configured to store information about diseases and/or disorders and classifications of such. For example, the knowledge base 30 may include health information chosen from mental disorders or illnesses and classification of mental disorders or illnesses. In certain embodiments, the knowledge base 30 is used by the server 12 when communicating with the patient 46 and/or users 48. For example, behavioral information captured from a patient through a variety of mechanisms (patient homework assignments, journals, messages, and the like) or input by a user and/or by a patient is processed by the server 12 as a function of the information provided by the knowledge base 30. Such information can be used, for example but not by way of limitation, to diagnose trends in a population of patients or identify a condition for a patient exhibiting particular symptoms.

The biological information repository 32 allows for the storage and retrieval of a patient's biological data. In certain embodiments, behavioral data is captured from a patient through a variety of mechanisms, transmitted to the application server 12, and stored in the repository 32. In certain non-limiting embodiments, the biological information is available to users 48 through the system interface 14, and may be used in the analysis of the patient information.

The rules database 34 is configured to store and retrieve remote healthcare communication system 10 rules. The rules are executed based on the content of one or more other database(s) (for example, but not by way of limitation, a patient's biological and behavioral data, illness thresholds, illness-type trends, geographical medical data, and results from previously-prescribed actions). The rules are configurable and maintainable by users 44 through the system interface 14.

The pharmacy records repository 36 allows for the storage and retrieval of a patient's pharmaceutical records and status. In certain embodiments, pharmaceutical data is captured from a variety of mechanisms (such as input from the patient 46, user 48, pharmacy, and the like) transmitted to the application server 12, and stored in the repository 36. In certain non-limiting embodiments, the pharmaceutical information is available to patients 46 and/or users 48 through the system interface 14, and may be used in the analysis of the patient information.

The health information exchange repository 38 allows for the mobilization of health care information electronically across organizations within a region, community, hospital system, or the like.

The laboratory repository 40 allows for the storage and retrieval of a patient's laboratory records and results. In certain embodiments, laboratory data is captured from a variety of mechanisms (such as input from the patient 46, user 48, laboratory testing, and the like) transmitted to the application server 12, and stored in the repository 40. In certain non-limiting embodiments, the laboratory information is available to patients 46 and/or users 48 through the system interface 14, and may be used in the analysis of the patient information.

In one non-limiting embodiment, at least some of the information from one or more database(s) 16 is available for access by the patient 46 and/or user 48 through the system interface 14, and may be used in the analysis of the patient information. In another non-limiting embodiment, the user 48 has access to a different amount and/or type of data than the patient 46. For example, but not by way of limitation, in one non-limiting embodiment, the user 48 may have access to one or more database that the patient 46 does not have access to. In another non-limiting embodiment, the patient 46 and/or user 48 may have less than full access to one or more database(s) 16.

System Interface 14

The remote healthcare communication system 10 includes the system interface 14 comprising the patient interface 42 and the user interface 44. Both the patient interface 42 and user interface 44 may include any number of human operators, computer systems (such as iPads, tablets, personal computers, and the like), mobile telephones, mobile computing devices, interactive voice response (IVR) systems, and any other suitable system and device for communicating with a patient(s) 46 and/or a user(s) 48. In one non-limiting embodiment, the system interface 14 is configured to allow the direct communication (through any suitable wired and/or wireless communication connection) between the server 12 and the patient 46 and/or the user 48.

The system interface 14 may additionally include any number of input devices (not shown). For example, the system interface may include a keyboard, mouse, touch pad, touch screen, alphanumeric keypad, voice recognition system, or other input device to allow the patient 46 and/or the user 48 to provide instructions and information to the medical data server 12. Similarly, the system interface 14 may include any number of suitable output devices (not shown), such as a monitor, speaker, printer, or other device.

Any type of information may be communicated through the system interface 14 by the patient 46 or the user 48 as discussed previously, such as the biological, biometric, or behavioral information for one or more patient(s). Information provided or received by the system interface 14 may be in any appropriate format. For example, an output device providing information to a user visually may provide patient information in the form of a series of measurements from different medical devices in a spreadsheet with headers indicating the source of the measurements. The system interface 14 can provide information in any number of desired languages, regardless of whether the information is provided audibly or visually.

Various features of the system interface 14 can be implemented in hardware, software, or a combination of the two. The system interface 14 can also provide and/or receive information to/from a user in a machine-readable format. The system interface 14 may interface with any suitable system or device, such as a thumb drive, memory stick, portable hard drive, an external computer system, or other USB-compatible device. The system interface 14 can be configured to send, receive, and process machine-readable data can in any standard format (such as a MS Word document, Adobe PDF file, ASCII text file, JPEG, or other standard format) as well as any proprietary format. Machine-readable data to or from the system interface may also be encrypted to protect the data from unintended recipients and/or improper use, as well as to comply with governmental regulations (such as HIPAA). Any other feature may be utilized in conjunction with the system interface 14 to allow a human or non-human user to interact with the server 12.

What is claimed is:

1. A remote healthcare system, comprising:
a user electronic device;
a patient electronic device having a patient interface for use by a patient and configured to establish a live audio-video session with the user electronic device;
the user electronic device having a user interface for use by a user and configured to establish a live audio-video session with the patient electronic device; and
an application server and system processor communicatively coupled with the patient electronic device and the user electronic device via a system interface, the application server and system processor coupled to a memory storing instructions that, when executed by the system processor, cause the application server and system processor to:
establish the live audio-video session between the patient and the user, wherein the user interface includes an augmented user interface including a patient viewing window showing a video representation of the patient, a user viewing window showing a video representation of the user, and at least one overlay user interface screen overlaying the patient viewing window such that at least a portion of the video representation of the patient is displayed, and
display at least one type of information about the patient and the live audio-video session on the at least one overlay user interface screen.

2. The remote healthcare system of claim 1, wherein the overlay user interface screen includes a user menu including one or more session options, the user menu and one or more session options being configured to allow the user to enter information into the overlay user interface screen and thereby document calls with the patient in real-time.

3. The remote healthcare system of claim 2, wherein the instructions, when executed by the system processor, cause the application server and the system processor to receive an instruction from the user electronic device, and then present on the patient interface, in a read-only format, at least a portion of the information entered into the overlay user interface screen.

4. The remote healthcare system of claim 2, wherein the memory stores one or more databases containing information forming a patient electronic health record for the patient, and wherein information entered into the overlay user interface screen is transmitted to the application server and stored in the memory as an update to the patient electronic health record for the patient.

5. The remote healthcare system of claim 4, wherein the patient has a support group having one or more support group members, and wherein one of the one or more databases is a connect database storing electronic contact information for the support group, and further comprising instructions that, when executed by the system processor, cause the application server and system processor to: establish a live audio session between the user and at least one of the one or more support group members using the electronic contact information stored in the connect database.

6. The remote healthcare system of claim 5, wherein the support group has at least two support group members, and wherein the connect database further stores information regarding a hierarchy of the support group members, and further comprising instructions that, when executed by the system processor, cause the application server and system processor to: establish a live audio session between the user and at least one of the support group members using the electronic contact information and the hierarchy stored in the connect database.

7. The remote healthcare system of claim 1, wherein the memory stores a flag for the patient indicating that the user is allowed to conduct sessions with the patient without a parent or legal guardian being present, and wherein the instructions that, when executed by the system processor, cause the application server and system processor to: read the flag stored in the memory and then establish the live audio-video session between the user and the patient without a presence of the parent or legal guardian.

8. The remote healthcare system of claim 4 wherein the instructions include a session documenter configured to capture and store still images of the live audio-video session, the still images including the patient viewing window and the user viewing window.

9. The remote healthcare system of claim 8, wherein the session documenter is configured to capture and store the still images at an interval.

10. The remote healthcare system of claim 9, wherein the interval of the session documenter is a predetermined interval.

11. The remote healthcare system of claim 9, wherein the interval of the session documenter at varying intervals.

12. The remote healthcare system of claim 8, wherein the session documenter is configured to embed an encryption key into the still images specific to the live audio-video session.

13. The remote healthcare system of claim 4, wherein the user is a first user, and the live audio-video session is a first live audio-video session of a treatment session for the patient, and wherein the instructions that, when executed by the system processor, cause the application server and system processor to: end the first live audio-video session of the treatment session for the patient, and establish a second live audio-video session between the patient and a second user as part of the treatment session for the patient, the first and second live audio-video sessions being substantially contiguous.

14. The remote healthcare system of claim 13, wherein the one or more databases stored in the memory including a billing database stores a first billing rate for the first user, and a second billing rate for the second user, and wherein the first live audio-video session encompasses a first time period stored in the billing database, and the second live audio-video session encompasses a second time period stored in the billing database, and wherein the instructions further issue an invoice including the first billing rate and the first time period, and the second billing rate and the second time period.

15. The remote healthcare system of claim 4, further comprising a first responder device having a first responder interface, and wherein the memory stores one or more databases containing information indicative of electronic contact information for at least one first responder associated with the patient, the patient electronic device having a device locator determining real-time location of the patient electronic device, and wherein the at least one of the patient interface or the user interface includes a crisis mechanism including instructions that cause the system processor to read the real-time location of the patient electronic device, read electronic contact information for the at least one first responder, and send a crisis message to the first responder device including an identity of the patient, and the real-time location of the patient electronic device.

* * * * *